US007943606B2

(12) United States Patent
Kiss

(10) Patent No.: US 7,943,606 B2
(45) Date of Patent: *May 17, 2011

(54) COMPOSITIONS AND METHODS TO CONTROL ABNORMAL CELL GROWTH

(75) Inventor: Zoltan Kiss, Austin, MN (US)

(73) Assignee: CanCure Laboratories, LLC, Austin, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/572,793

(22) Filed: Oct. 2, 2009

(65) Prior Publication Data

US 2010/0048668 A1 Feb. 25, 2010

Related U.S. Application Data

(62) Division of application No. 12/501,895, filed on Jul. 13, 2009, which is a division of application No. 11/458,502, filed on Jul. 19, 2006, now Pat. No. 7,589,083.

(60) Provisional application No. 60/716,346, filed on Sep. 12, 2005.

(51) Int. Cl.
*A61K 31/382* (2006.01)
*C07D 335/16* (2006.01)

(52) U.S. Cl. .......................................... 514/183; 549/27

(58) Field of Classification Search .................. 514/183; 549/27

See application file for complete search history.

(56) References Cited

U.S. PATENT DOCUMENTS

| 2,512,520 | A | 6/1950 | Cusic |
| 2,590,125 | A | 3/1952 | Robinson et al. |
| 4,183,912 | A | 1/1980 | Rosenthale |
| 2003/0212061 | A1 | 11/2003 | Haydar |

FOREIGN PATENT DOCUMENTS

| DE | 844154 C | 7/1952 |
| EP | 0224967 A1 | 6/1987 |
| EP | 1066813 A2 | 1/2001 |
| WO | WO 98/49172 A1 | 11/1998 |

OTHER PUBLICATIONS

Kinart, Wojciech J. et al., "The Electrochemical Studies on Five Water-Soluble Polymerization Initiations Based on the Thioxanthone Structure", Phosphorus, Sulfur and Silicon and the Related Elements, Taylor & Francis, US, vol. 59, No. 1-4, Jan. 1, 1991, pp. 215-218.
Bratt, P. et al., :"Photoionization of Neutral and Positively Charged Alkylphenothiazines in Positive, Neutral and Negatively Charged Vesicles: Effects of the Alkyl Chain Length", Journal of Physical Chemistry, vol. 95, No. 17, 1991, pp. 6400-6402.
Mesa-Valle, C.M. et al., "Activity and Mode of Action of Acridine Compounds Against Leishmania Donovani", Antimicrobial Agents and Chemotherapy, vol. 40, No, 3, 1996, pp. 684-690.
Blanz, E. J. et al., "A Systematic Investigation of Thioxanthen-9-Ones and Analogs as Potential Antitumor Agents", Journal of Medicinal Chemistry, American Chemical Society, Washington, US, vol. 6, Mar. 1, 1963, pp. 155-191.
Greene, T.W., et al,, "Protective Groups in Organic Synthesis", 1999, John Wiley & Sons, Quaternary Ammonium Salts, pp. 578-579.
Ghezzi, Pietro et al., "Mechanism of Inhibition of Tumor Necrosis Factor Production by Chlorpromazine and its Derivatives in Mice", European Journal of Pharmacology, vol. 317, No. 2-3, Jan. 1, 1996, pp. 370-372.
Qian et al., "Photochemistry Study on New Water Soluble Thioxanthone", *Guangpuxue Yu Guangpu Fenxi*, vol. 20, No, 6, 2000, pp. 807-809.
Lin et al., "Synthesis of Water Soluble Photoinitiators of Thioxanthone Derivatives III" *Huadong Ligong Daxue Xuebao*, vol. 26, No. 2, 2000, pp. 212-214, 220.
Lin et al., "Syntheses and properties of Water Soluble Thioxanthone Photoinitiators", *Yingyong Huaxue*, vol. 16, No. 5, 1999, pp. 25-28.
Supplementary European Search Report issued in EP App 06787717, mailed May 26, 2010, 13 pages.

*Primary Examiner* — Taofiq A Solola
(74) *Attorney, Agent, or Firm* — Faegre & Benson LLP

(57) ABSTRACT

A class of compounds commonly containing a trialkylammonium group have been synthesized and characterized as anti-cancer compounds. They can be used alone or in combination with other therapies to treat cancer and other cell proliferative diseases. Representative compounds of this class, N,N-diethyl-N-methyl-2-[(9-oxo-9H-thioxanthen-2-yl)methoxy]ethanaminium iodide and N,N-diethyl-N-allyl-3-(2-methyl-9H-thioxanthen-9-ylidene)-propane-1-aminium bromide, were shown in various tumor models to decrease tumor volume, enhance the effects of other chemotherapeutic agents including cisplatin, reduce chemotherapy-induced loss of body weight, and increase survival of animals co-treated with toxic amounts of cisplatin. These compounds had even greater effects on tumor volume, body weight, and survival when administered together with the human protein placental alkaline phosphatase.

17 Claims, 16 Drawing Sheets

COMPOSITIONS AND METHODS TO CONTROL ABNORMAL CELL GROWTH

CROSS REFERENCE TO RELATED APPLICATION

The present application is a divisional of U.S. application Ser. No. 12/501,895, filed Jul. 13, 2009, which is a divisional of U.S. Pat. No. 7,589,083, filed Jul. 19, 2006, which claims the benefit of U.S. Provisional Application 60/716,346, filed Sep. 12, 2005, all of which are incorporated herein by reference.

I. FIELD OF THE INVENTION

Embodiments of this invention include the use of a specific class of chemically synthesized compounds and alkaline phosphatase, separately or in combination with each other and other therapies, to selectively decrease the viability of non-healthy cells, particularly cancer cells in tumors that lost growth control. Other embodiments of the invention also use these chemically synthesized compounds and alkaline phosphatase to enhance the efficacy of chemotherapy with simultaneous reduction of side effects.

II. BACKGROUND

Over a lifetime there is a potential for the development of many different types of proliferative diseases in solid tissues characterized by the loss of cellular growth control, such as cancer, psoriasis, or keloid tissue. The diseased tissues and organs are often characterized by either higher than normal rate of proliferation of the affected cells (usually at the expense of the surrounding normal cells) or the inability to stop proliferating when so signaled by appropriate signaling mechanisms often activated by differentiation-inducing agents. Since in unhealthy and healthy tissues expression of various genes usually differs only quantitatively but not qualitatively, it is extremely difficult to employ a particular kind of chemotherapy that selectively destroys only the non-healthy tissue. This is one reason that only few effective monotherapies exist against any of these diseases that would be relatively free of toxic side effects.

Therefore, in recent years various combination chemotherapies have become standard procedures to attack these proliferative diseases, particularly cancers. While combination therapies are usually more effective than treatments with single agents, they are often even more toxic than monotherapies that usually act via a single mechanism. Thus, it would be desirable to develop new anti-proliferative agents that add to the effects of known chemotherapies and simultaneously decrease the usual side effects such as significant weight loss accompanied by fatigue. For that purpose, embodiments of the present invention provide a class of chemically synthesized agents and alkaline phosphatase, particularly the placental type alkaline phosphatase, both alone or in combination.

SUMMARY OF THE INVENTION

Embodiments of this invention include simultaneously enhancing the efficacy and decreasing the toxicity of chemotherapy by single agents and particularly their combinations. These agents are also suitable to enhance the efficacy of other therapies aimed at selectively suppressing the growth of non-healthy cells and tissues characterized by uncontrolled growth.

Finally, other embodiments of the invention include a class of chemically synthesized compounds that, even when used as single agents, exert strong anti-cancer effects, for example, against ovarian, breast cancer, and other types of cancer cells.

The first class of agents used in embodiments of the invention are chemically synthesized. They were designed to inhibit cellular choline transport across the cell membrane and alter the membrane potential of mitochondria. Both of these effects of chemically synthesized compounds (hereinafter referred to as "CC compounds") are directed at non-healthy cells with some specificity. A third separate mechanism of action in vivo, specifically accounting for the ability of CC compounds to decrease or prevent chemotherapy-induced reduction in body weight, is very likely. Representatives of CC compounds are CCompound3 (or CCDTHT) and CCompound26, although the effects of several more of these compounds are presented in embodiments of the invention.

In one embodiment, the invention provides for preferential killing of non-healthy abnormally growing cells, in vitro, by CC compounds. In other embodiments, the invention provides methods to employ CCompound3 or CCDTHT and other CC compounds in humans and other mammals to decrease the growth of abnormally growing tissues (including tumor tissues), normalize body weight, and decrease the toxic side effects caused by chemotherapy or other therapies. CCompound3, CCompound26 and most other CC compounds are soluble in water and are suitable for oral application in the form of tablets, gel capsules and the like. They also can be administered by one of the available systemic routes.

The second agent used in embodiments of the invention is placental alkaline phosphatase (PALP), a member of the alkaline phosphatase family. In one embodiment, the invention provides methods to employ PALP and other alkaline phosphatases in humans and other mammals to enhance the efficacy of various treatments aimed at decreasing the growth of abnormally growing tumor tissues. The terms "PALP" and "alkaline phosphatase" are used interchangeably throughout the application. In another embodiment, PALP is used to normalize body weight and decrease the toxic side effects caused by chemotherapy and other treatments. Alkaline phosphatases can be applied for therapy via injection using one of the available systemic routes.

Embodiments of the invention also provide for the use of CCompound3 and other CC compounds as well as PALP and other alkaline phosphatases in combination to more effectively enhance the effects of other therapies to control tumor growth as well as restore body weight and decrease therapy-induced toxic side effects.

μM CCDTHT (CCompound3) for 72 hours in 12-well plates were all rounded up, indicating death via one of the apoptotic pathways (B).

FIGS. 5A-5F compare the anti-cancer effects of 50-200 μM concentrations of commercially available CCompound1 (●) as well as CCDTHT (CCompound3) (▲) on the viability of NIH 3T3, MEL-28, A549, HT-29, A-431 and MCF-7 cells after treatments for 72 hours.

Figure 6:
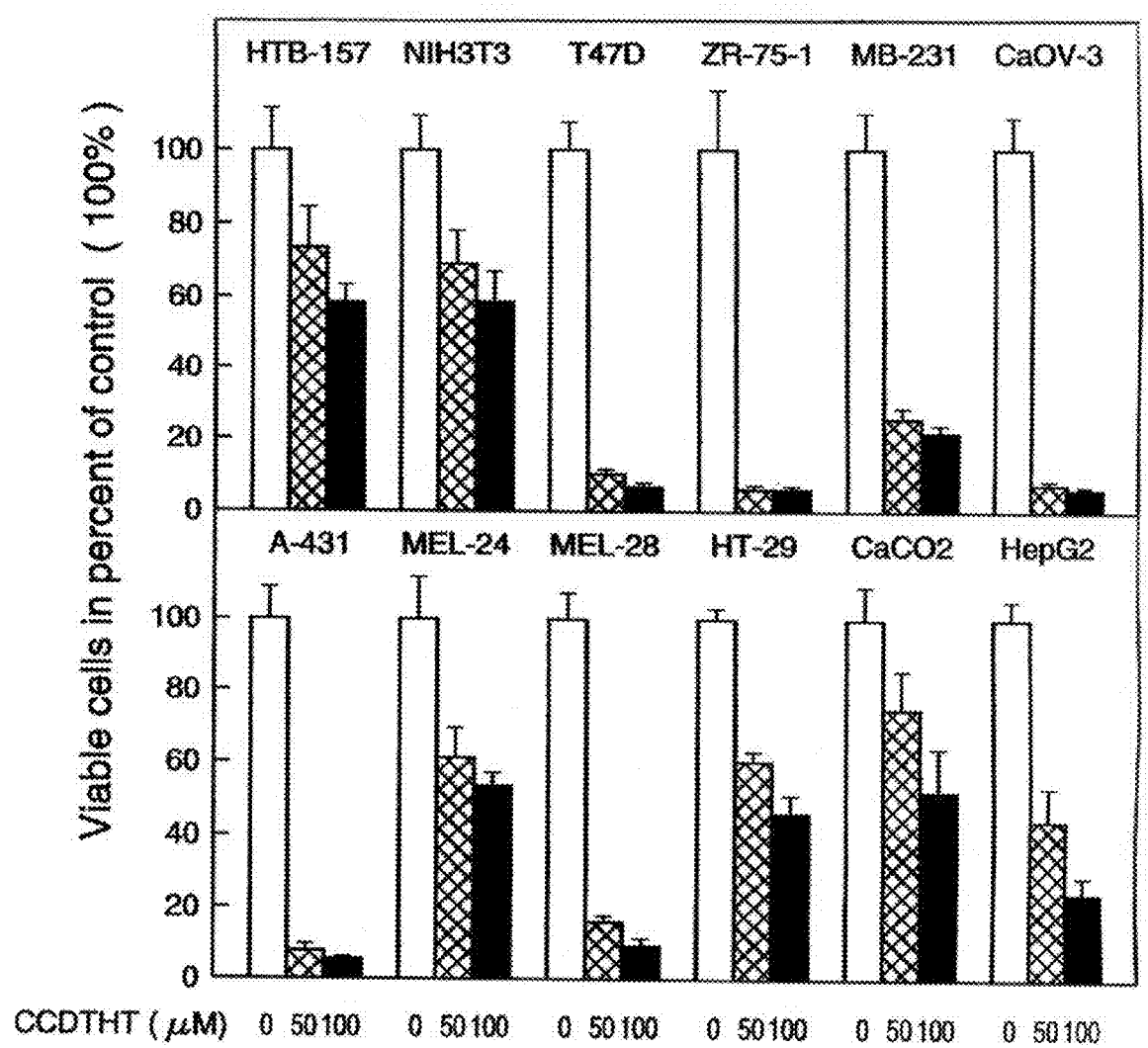

FIG. 6 shows the effects of 50 μM and 100 μM CCDTHT on cell viability in the normal HTB-157 and NIH 3T3 fibroblasts as well as 10 established cancer cell lines including T47D, ZR-75-1, MB-231, CaOV-3, A-431, MEL-24, MEL-28, HT-29, CaCO-2, and HepG2 cells after continuous treatments for 10 days.

Figure 7:
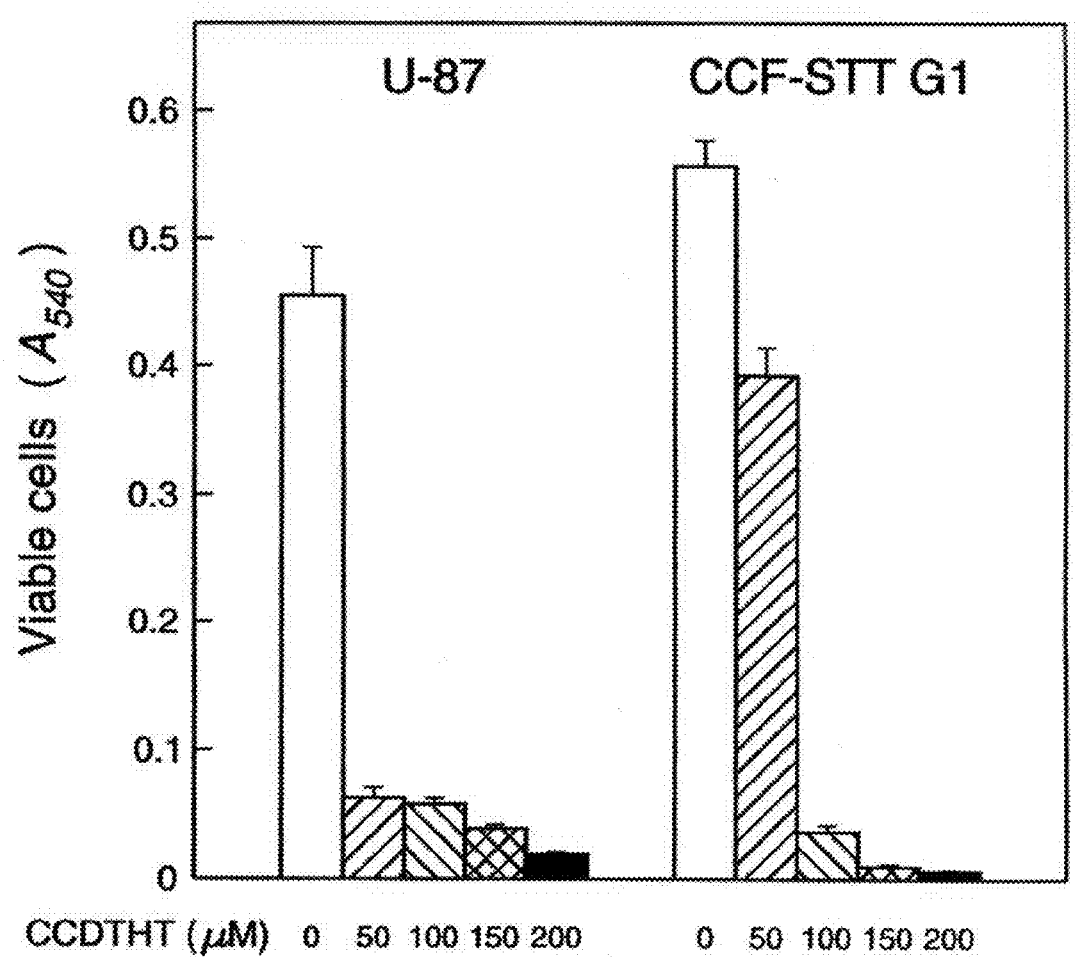

FIG. 7 shows the effects of 5, 100, 150 and 200 μM CCDTHT on the viability of U-87 and CCF-STT G1 cancer cells after treatments for 72 hours.

Figure 8:
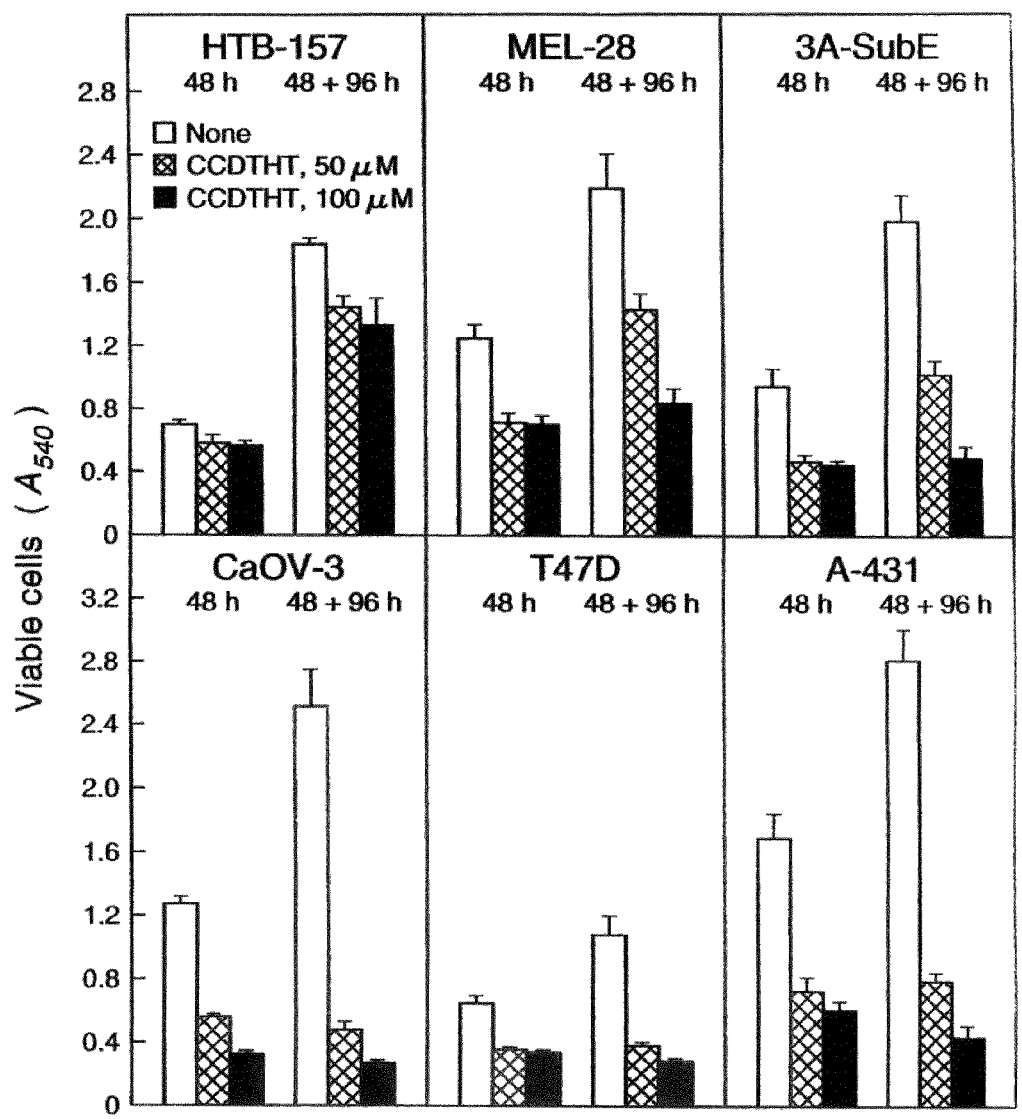

FIG. 8 depicts an experiment performed with six different types of cells. HTB-157, MEL-28, 3A-SubE, CaOV-3, T47D and A-431 cells were first treated for 48 hours with 50 μM or 100 μM CCDTHT (48 h) and then incubated in fresh medium (in the absence of CCDTHT) for 96 hours (48+96 h); the relative numbers of viable cells are shown.

Figure 9:
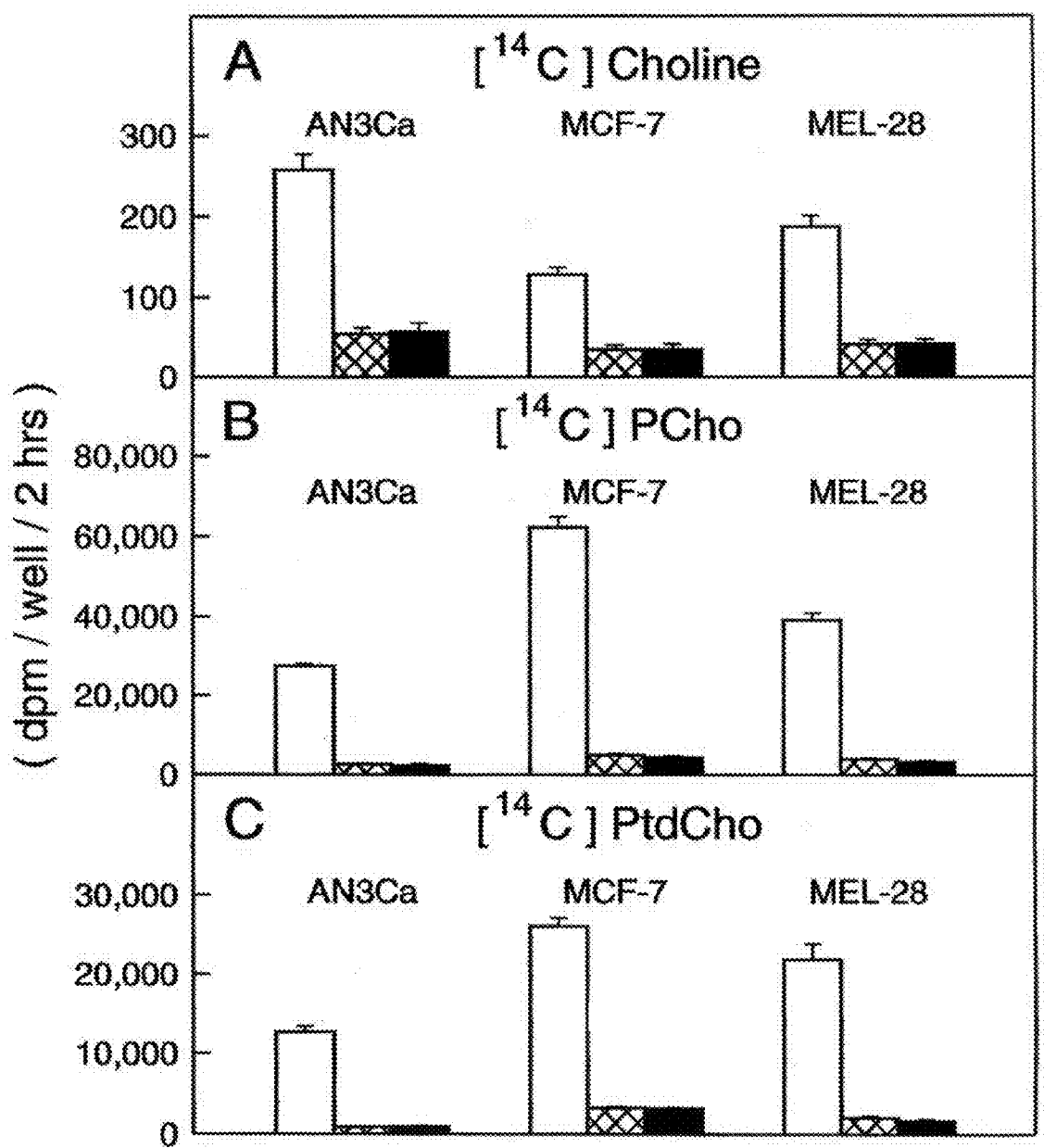

FIG. 9 shows that in the AN3CA MCF-7 and MEL-28 human cancer cells, 100 μM CCDTHT (☒)and 0.5 mM HC-3 (■) exerted similarly strong inhibitory effects on the cellular uptake of [$^{14}$C]choline (A) as well as on the synthesis of [$^{14}$C]PCho (B) and [$^{14}$C]PtdCho (C) from radiolabeled choline after treatments for 2 hours. The symbol "□" represents the corresponding values in the untreated cells.

Figure 10:
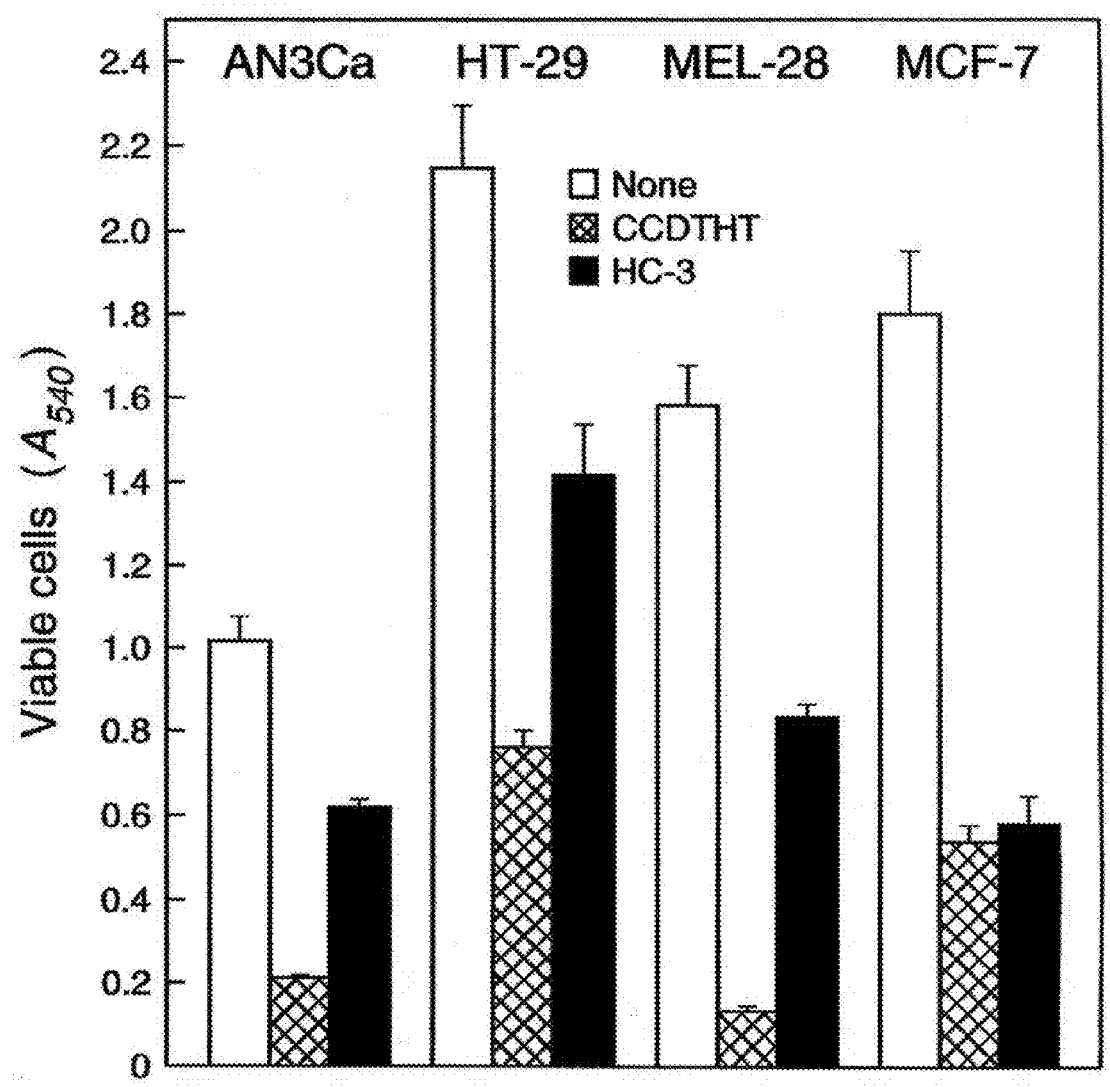

FIG. 10 demonstrates that in AN3CA, HT-29 and MEL-28 cancer cells, but not in MCF-7 cancer cells, 100 μM CCDTH (☒)caused a much larger decrease in the number of viable cells than 0.5 mM HC-3 did (■) after treatments for 72 hours. The symbol "□" represents the corresponding viability values in the untreated cells.

Figure 11:
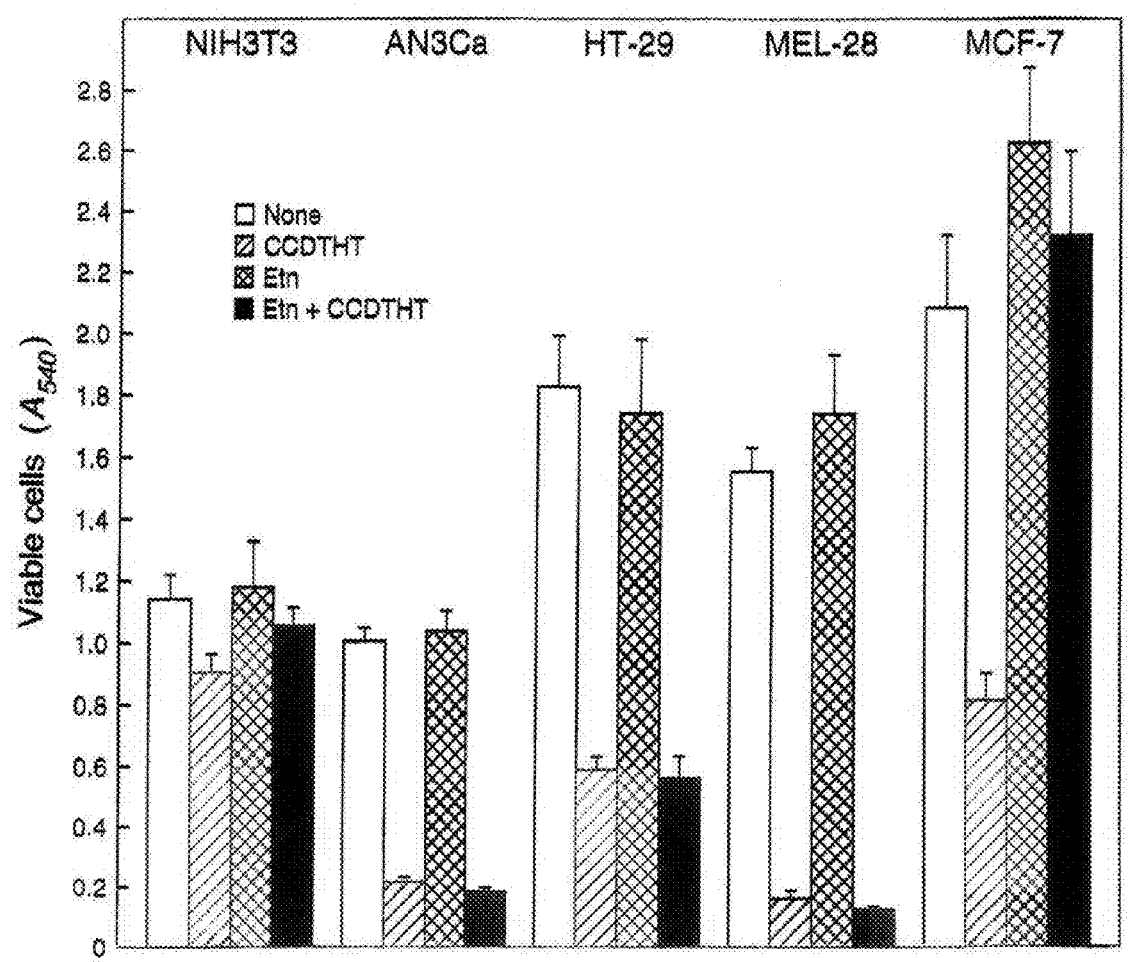

FIG. 11 shows that in MCF-7 cells, but not in AN3CA, HT-29, or MEL-28 cells, 2 mM ethanolamine (Etn) prevented the large decrease in viability induced by 100 μM CCDTHT after treatments for 72 hours. In the NIH3T3 non-cancerous cells CCDTHT had no significant effects either in the absence or presence of Etn.

Figure 12:
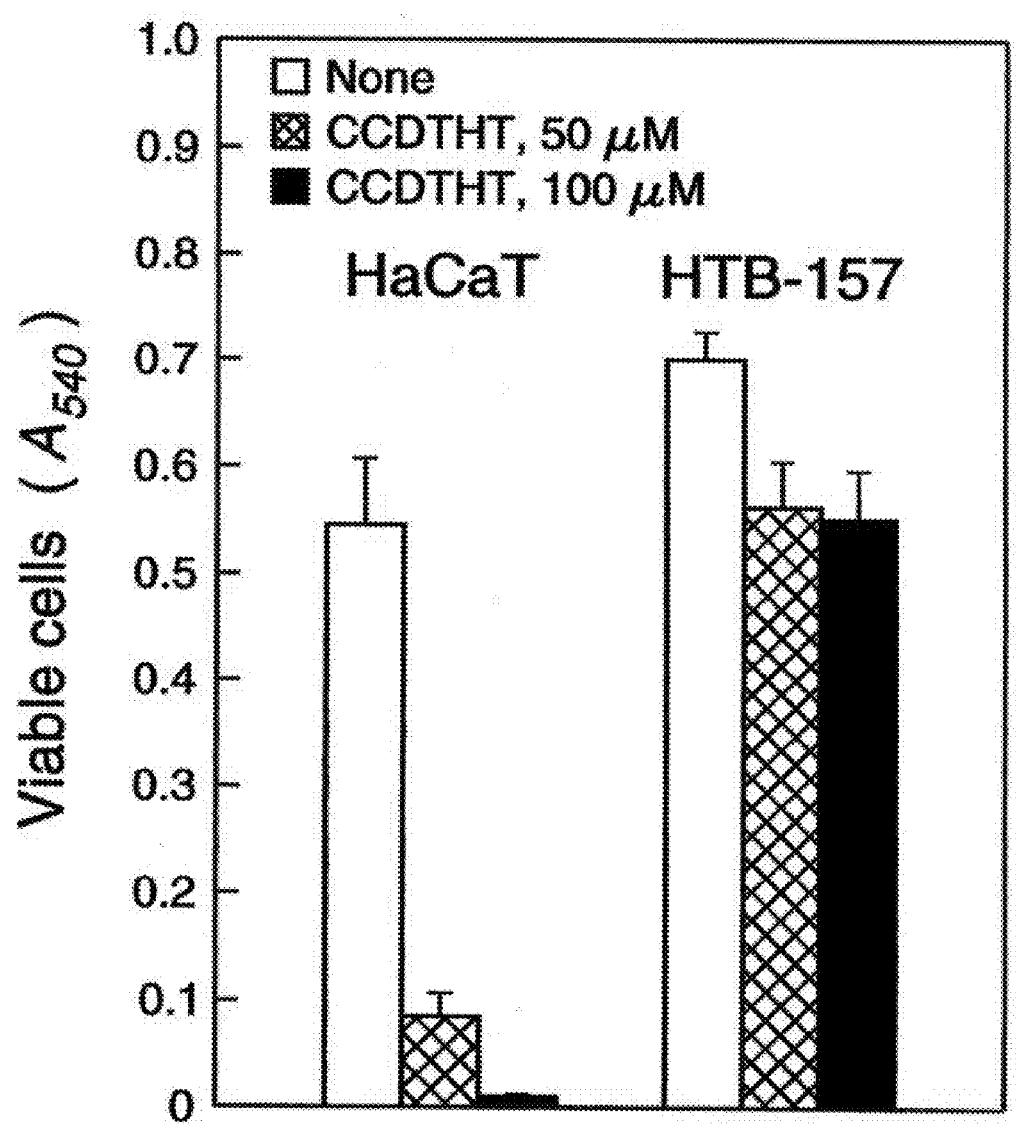

FIG. 12 shows that treatments of HaCaT keratinocytes with 50 μM or 100 μM CCDTHT for 48 hours resulted in the death of 85-100% of cells. Similar treatments of HTB-157 fetal (normal) fibroblasts with CCDTHT caused only 19-20% inhibition of cell proliferation.

Figure 13:
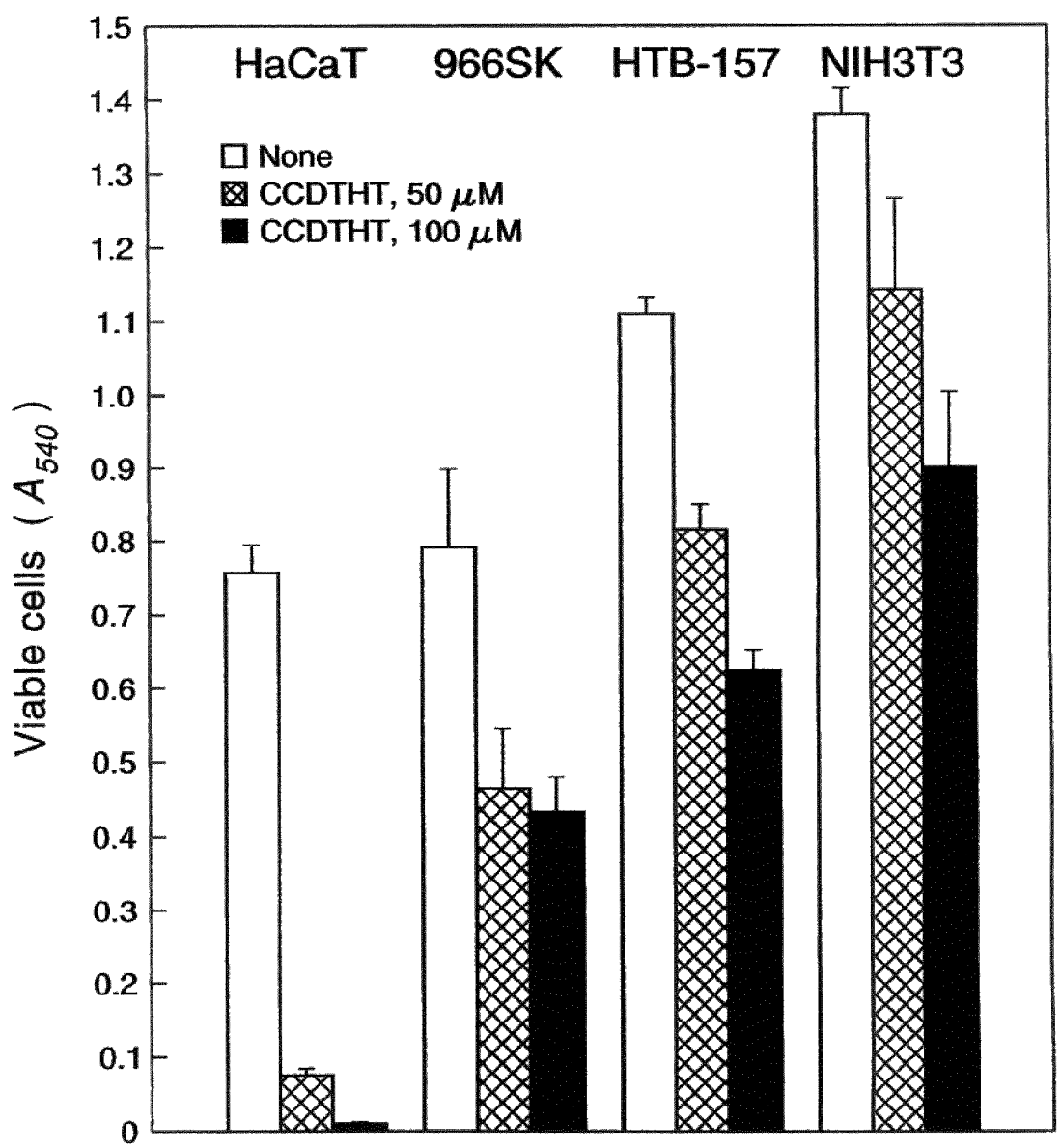

FIG. 13 shows an experiment in which the effects of 50 μM and 100 μM CCDTHT were compared on the viability of HaCaT cells as well as 966 SK, HTB-157, and NIH 3T3 normal fibroblasts after treatments for 72 hours.

Figure 14:
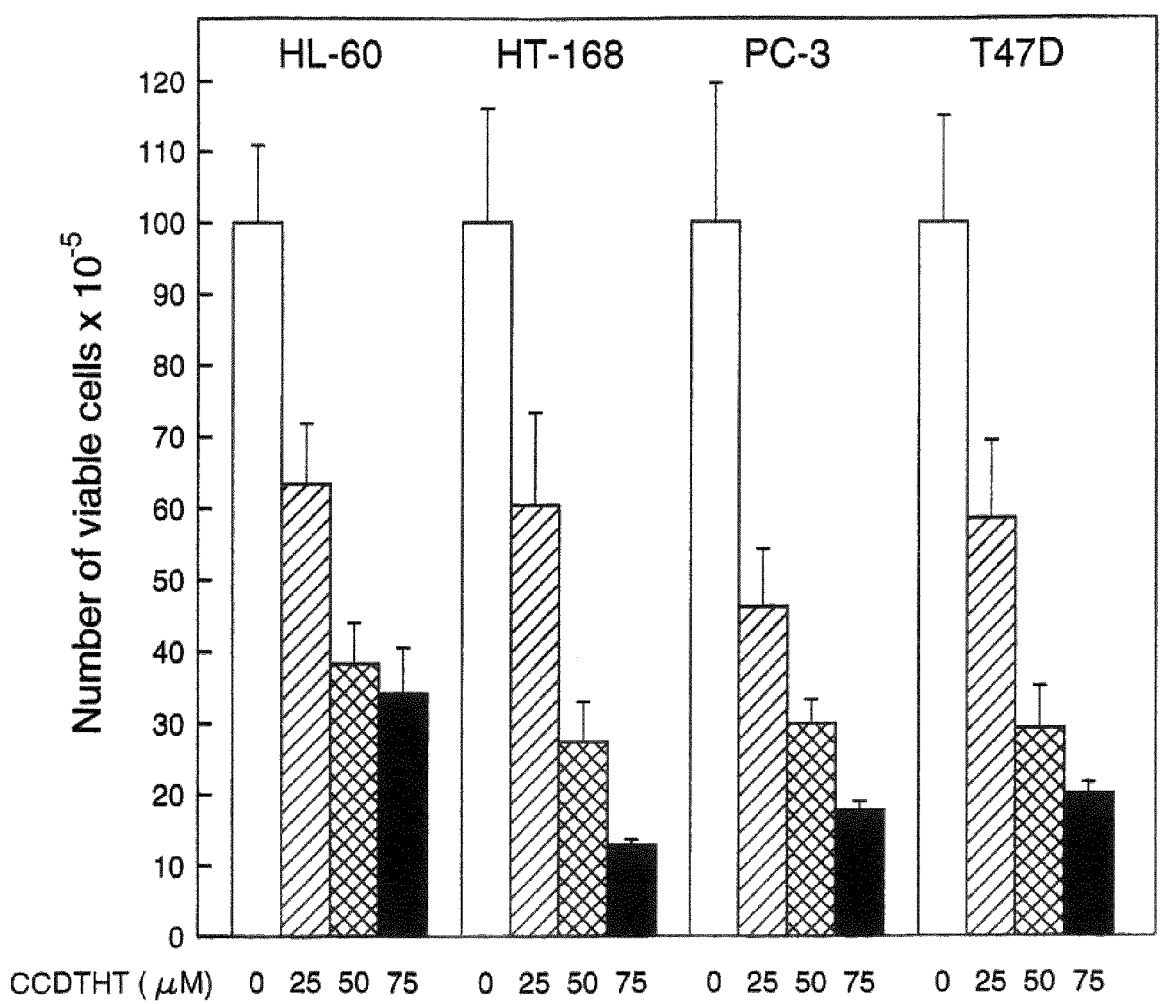

FIG. 14 shows that in human leukemia HL60 cells, human melanoma HT-168 cells, human prostate cancer PC-3 cells and human breast cancer T47D cells 25 μM CCDTHT inhibited cell proliferation by ~40-55%, while 75 μM CCDTHT decreased the number of viable cells by ~65-85% if treatments were for 96 hours.

Figure 15:
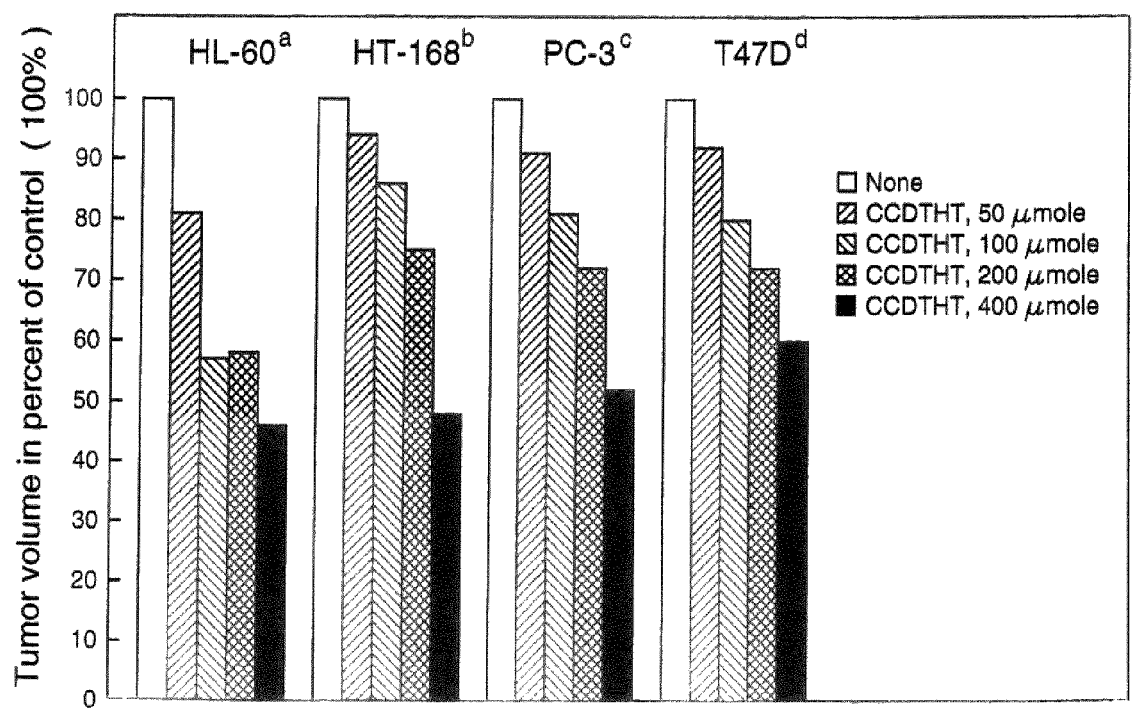

FIG. 15 depicts the effects of 50 μmole (◨), 100 μmole (▨), 200 μmole (☒), and 400 μmole CCDTHT (■), injected subcutaneously, on the growth of HL-60 (leukemia), HT-169 (melanoma), PC-3 (prostate), and T47D (breast) human tumor xenografts. The symbol "□" indicates the corresponding values in the untreated cells. In a, b, c, d treatments started on day 18, 17, 12 and 17, respectively; once daily treatments were performed for 5+3 days, 5+5 days, 5+3 days and 5+5 days, respectively, in each case with two treatment-free days between the two treatment series. The values represent tumor size measured one day after the last treatment.

Figure 16:
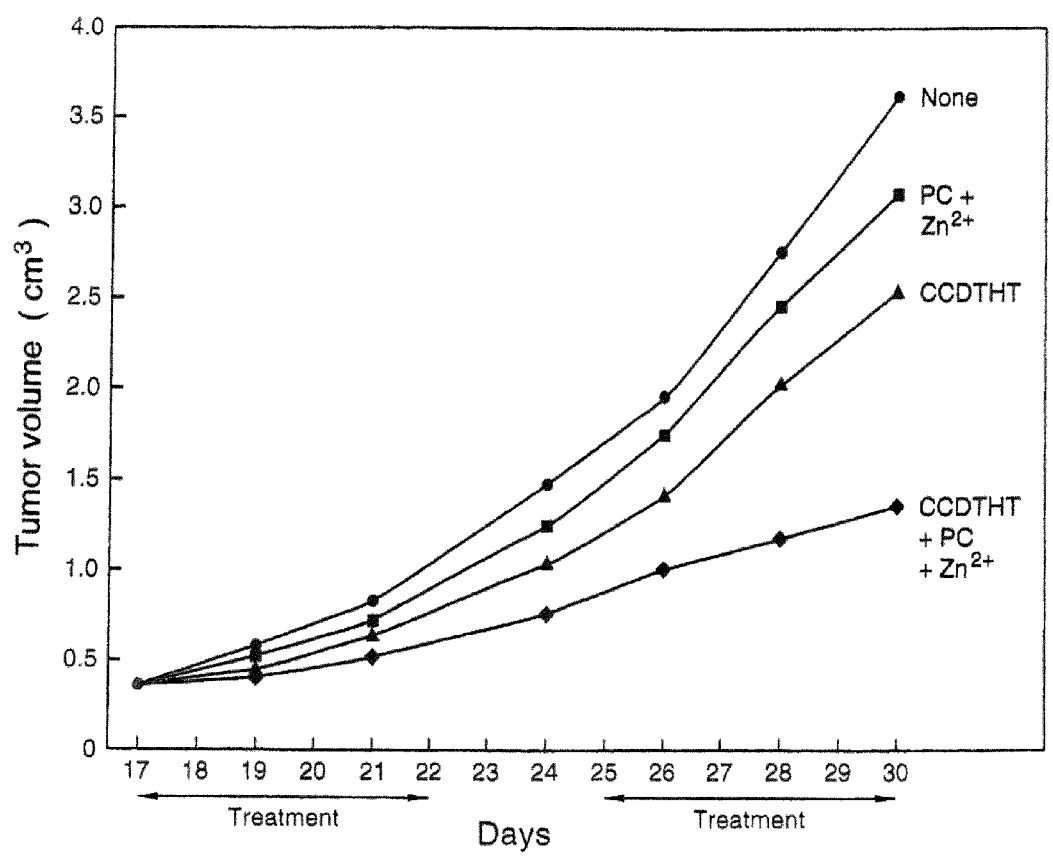

FIG. 16 demonstrates the growth of human melanoma HT-168 xenografts between 17-30 days with no treatment (●), or with once daily treatments on days 17, 18, 19, 20, 21, 24, 25, 26, 27 and 28 with 200 μmole CCDTHT (▲), 100 μmole pyrrolidinedithiocarbamate (PC)+100 μmole zinc chloride (Zn) (■), or 200 μmole CCDTHT+100 μmole PC+100 μmole Zn (♦).

DETAILED DESCRIPTION OF THE INVENTION

Mitochondria in cancer cells are characterized by significantly higher membrane potential than normal cells due to a high negative charge. Positively charged compounds can pass through the hydrophobic barrier of a cell (plasma) membrane, particularly if they are sufficiently hydrophobic, but they are retained in the mitochondrial membrane due to the negative charge of the latter. This can affect the function of mitochondria and lead, eventually, to cell dead. A well established prototype of such a positively charged compound is rhodacyanine MKT 077 or 1-ethyl-2-{[3-ethyl-5-(3-methylbenzothiazolin-2-yliden]-4-oxothiazolidin-2-ylidenemethyl}pyridium chloride [Kawakami, M., Koya, K., Ukai, T., Tatsuta, N., Ikegawa, A., Ogawa, K., Shishido, T. and Chen, L. B. (1998), "Structure-activity of novel rhodacyanine dyes as antitumor agents," J. Med. Chem. 41, 130-142; Chiba, Y., Kubota, T., Watanabe, M., Otani, Y., Teramoto, T., Matsumoto, Y., Koya, K. and Kitajima, M. (1998), Selective antitumor activity of MKT-077, a delocalized lipophilic cation, on normal cells and cancer cells in vitro," J. Surgical Oncol. 69, 105-110]. Unfortunately, phase I human trials revealed that MKT 077 exerts significant renal toxicity which prevents its use in human subjects [Propper, D. J., Braybrooke, J. P., Taylor, D. J., Lodi, R., Styles, P., Cramer, J. A., Collins, W. C. J., Levitt, N. C., Talbot, D. C., Ganesan, T. S. and Harris, A. L. (1999), "Phase I trial of the selective mitochondrial toxin MKT 077 in chemo-resistant solid tumours: Annals of Oncol. 10, 923-927; Britten, C. D., Rowinsky, E. K., Baker, S. D., Weiss, G. R., Smith, L., Stephenson, J., Rothenberg, M., Smetzer, L., Cramer, J., Collins, W., Von Hoff, D. D. and Eckhardt, S. G. (2000), "A phase I and pharmacokinetic study of the mitochondrial-specific rhodacyanine dye analog MKT 077," Clin. Cancer Res. 6, 42-49]. Evidently, a positively charged compound which has the potential to interact with and decrease the membrane potential of mitochondria would be expected to effectively inhibit proliferation of cells with some specificity toward cancer cells. In embodiments of this invention, various molecules ("CC compounds") that have both hydrophobic and hydrophilic moieties with a net positive charge may kill abnormal cells, including cancer cells, in vitro and in vivo.

Recent research has revealed that cancer cells exhibit high choline kinase activity, an enzyme that produces phosphorylcholine (PCho, also known as choline phosphate) from the choline and adenosinetriphosphate precursors. For that reason, direct inhibitors of choline kinase exhibit anti-cancer activity in various in vivo tumor models [Hernandez-Alcoceba, R., Fernandez, F. and Lacal, J. C. (1999), "In vivo antitumor activity of choline kinase inhibitors: A novel target for anticancer drug discovery," Cancer Res. 59, 3112-3118; de Molina, A. R., Gutierrez, R., Ramos, M. A., Silva, J. M., Silva, J., Bonilla, F., Sanchez, J. S. and Lacal, J. C. (2002), "Increased choline kinase activity in human breast carcinomas: clinical evidence for a potential novel antitumor strategy," Oncogene 21, 4317-4322]. Another possible mechanism to decrease the synthesis of PCho is via inhibiting choline uptake system in the target cells. Rapidly proliferating cells, such as most cancer cells, have higher choline transport capacity than normal cells to satisfy the need of phosphatidylcholine (PtdCho) biosynthesis for this precursor. PtdCho is a major phospholipid that is an essential building block of biological membranes. Therefore, any disruption of PtdCho synthesis will have a negative impact on cell proliferation. Accordingly, inhibitors of choline transport are expected to preferentially inhibit rapid proliferation of non-healthy cells in vivo with less impact on normal tissues. Based on these considerations, the CC compounds were designed to contain moieties that can interfere with cellular uptake of choline from the extracellular milieu in addition to reducing membrane potential in the mitochondria.

There are two different transport systems for choline. The sodium-dependent, high-affinity transport system is specifically localized to cholinergic nerve terminals and provides choline for acetylcholine synthesis. The low-affinity choline transport system is present in most cell types, including those dealt with in embodiments of the present invention, and provides choline for the synthesis of PCho and PtdCho [Slack, B. E., Breu, J., Livneh, E., Eldar, H. and Wurtman, R. J. (1995), "Phorbol ester stimulates choline uptake in Swiss 3T3 fibroblasts following introduction of the gene encoding protein kinase Cα, Biochem. J. 305, 621-626; and references therein]. Hemicholinium-3, or HC-3 [2,2'-(4,4'-biphenylene)-bis(2-hydroxy-4,4-dimethylmorpholinium bromide], is a more effective inhibitor of the high-affinity choline transport system, compared to the low-affinity system, resulting in the depletion of acetylcholine stores. For this reason, HC-3 and some related bis-hemiketal compounds are toxic causing delayed and progressive respiratory failure [Happe, H. K. and Murrin, L. C. (1993), "High-affinity choline transport sites: Use of [$^3$H]hemicholinium-3 as a quantitative marker," J. Neurochem. 60, 1191-1201; Cannon, J. G. (1994), "Structure-activity aspects of hemicholinium-3 (HC-3) and its analogs and congeners," Medicinal Res. Rev. 14, 505-531]. Clearly, for inhibiting PCho and PtdCho synthesis in rapidly growing aberrant cells, it would be necessary to use a choline transport inhibitor that, unlike HC-3, is non-neurotoxic (or significantly less toxic); i.e. that preferentially inhibits the low-affinity transport system. CC compounds in embodiments of the present invention are sufficiently different from HC-3 to have less toxicity, but they also contain a group that has the ability to compete with choline for the low affinity transport system. Because CC compounds contain a positive charge (due to the quaternary ammonium), these compounds also only poorly penetrate, if at all, the brain-blood barrier that further decreases their potential inhibitory effects on neurotransmission.

The choline transport system in rapidly proliferating cells, particularly cancer cells, is more abundant than in normal cells. Since the concentration of choline in the blood is only around 25 µM, the rapidly growing tumor tissue will use most of the choline with little choline left for the normal cells. However, since in most normal established tissues only a very low level of cell proliferation is going on, these tissues can survive and function normally even at very low blood choline levels. Thus, it was expected that concentrations of CC compounds that inhibit tumor growth via inhibiting choline uptake should have no or much less toxic effects in normal tissues.

It was reported earlier that placental alkaline phosphatase (PALP), one of the presently known four members of the alkaline phosphatase enzyme family [J. L. Millan and W. H. Fishman (1995), "Biology of human alkaline phosphatases with special reference to cancer," Critical Reviews in Clinical Sciences 32, 1-39], can enhance both the proliferation and survival of mouse embryo fibroblasts as well as fibroblast-like cells derived from the lung of human fetus [Q.-B. She, J. J. Mukherjee, J.-S. Huang, K. S. Crilly, and Z. Kiss (2000), "Growth factor-like effects of placental alkaline phosphatase in human fetus and mouse embryo fibroblasts," FEBS Letters, 468, 163-167; Q.-B. She, J. J. Mukherjee, T. Chung, and Z. Kiss (2000), "Placental alkaline phosphatase, insulin, and adenine nucleotides or adenosine synergistically promote long-term survival of serum-starved mouse embryo and human fetus fibroblasts," Cellular Signalling 12, 659-665]. In two recent U.S. patent applications filed by the present inventor, PALP was shown to also enhance proliferation of human fibroblasts [U.S. Pat. No. 7,011,965, entitled "Compositions and Methods for Stimulating Wound Healing and Fibroblast Proliferation"; U.S. patent application Ser. No. 10/653,622, filed Sep. 2, 2003 and entitled "Use of Placental Alkaline Phosphatase to Promote Skin Cell Proliferation"]. In both patent applications, the effects of PALP alone on wound healing and skin care applications are reported.

In the present application, PALP is used either alone or in combination with a CCompound and/or other chemotherapeutic agents to decrease tumor growth and restore chemotherapy-induced loss of body weight. For this, PALP was highly purified from commercial (Sigma-Aldrich) PALP prepared by a previously described method with minor modifications [Q.-B. She, J. J. Mukherjee, J.-S. Huang, K. S. Crilly, and Z. Kiss (2000), "Growth factor-like effects of placental alkaline phosphatase in human fetus and mouse embryo fibroblasts," FEBS Letters, 468, 163-167]. Analysis by gel electrophoresis and peptide analysis shows that in the PALP preparations purchased from Sigma-Aldrich, PALP represents about 10% of the total protein, the remaining being represented by $\alpha_1$-antitrypsin, transferrin, albumin, and few other lower molecular mass contaminating proteins mostly derived from transferrin.

The alkaline phosphatase family also includes the tissue non-specific (liver/bone/kidney) alkaline phosphatase, the intestinal alkaline phosphatase, and the PALP-like (germ-cell) alkaline phosphatase. Since each of these enzymes has similar phosphatase activities that may contribute to the negative control of cancer cell growth, these three enzymes may share, at least partially, the anti-cancer effects of PALP.

Amifostine is one of the few non-growth factor agents that may provide some protection against the toxic effects of chemotherapy in specific cases [for example, Verstappen, C. C. P., Postma, T. J., Geldof, A. A. and Heimans, J. J. (2004), "Amifostine protects against chemotherapy-induced neurotoxicity: An in vitro investigation,"Anticancer Res. 24, 2337-2342; Kemp, G., Rose, P., Lurain, J., Berman, M., Manetta, A., Roullet, B., Homesley, H., Belpomme, D. and Glick, J. (1996), "Amifostine pretreatment for protection against cyclophosphamide-induced and cisplatin-induced toxicities: Results of a randomized control trial in patients with advanced ovarian cancer," J. Clin. Oncol. 14, 2101-2112] and radiation therapy [Brizel, D. M., Wasserman, T. H., Henke, M., Strnad, V., Rudat, V., Monnier, A., Eschwege, F., Zhang, J., Russell, L., Oster, W. and Sauer, R. (2000), "Phase III randomized trial of amifostine as a radioprotector in head and neck cancer," J. Clin. Oncol. 18, 3339-3345]. Apart from the fact that amifostine often causes side effects such as nausea, vomiting, hypotension and allergic reaction, an even more serious concern is that it may actually enhance the survival of tumor cells in vivo [Verstappen, C. C. P., Postma, T. J., Geldof, A. A. and Heimans, J. J. (2004), "Amifostine protects against chemotherapy-induced neurotoxicity: An in vitro investigation," Anticancer Res. 24, 2337-2342]. Other agents that may provide some protection against specific chemotherapeutic agents include the flavonoid Frederine [van Acker, F. A. A., Boven, E., Kramer, K., Haenen, G. R. M. M., Bast, A. and van der Vijgh, W. J. F. (2001), "Frederine, a new and promising protector against doxorubicin-induced cardiotoxicity," Clin. Cancer Res. 7, 1378-1384], glutamine [Vahdat, L., Papadopoulos, K., Lange, D., Leuin, S., Kaufman, E., Donovan, D., Frederick, D., Bagiella, E., Tiersten, A., Nichols, G., Garrett, T., Savage, D., Antman, K., Hesdoffer, C. S. and Balmaceda, C. (2001), "Reduction of paclitaxel-induced peripheral neuropathy with glutamine," Clin. Cancer Res. 7, 1192-1197], and salicylate [Li, G., Sha, S.-H., Zotova, E., Arezzo, J., van de Water, T. and Schacht, J. (2002), "Salicylate protects hearing and kidney function from cisplatin toxicity without compromising its oncolytic action," Lab. Invest. 82, 585-596].

Among the known growth-regulatory agents, Granulocyte colony stimulating factor, interleukin-6, and erythropoietin or Darbapoetin alfa act to normalize blood cell counts which then helps to overcome chemotherapy-related or other cancer-therapy-related fatigue. Unfortunately, all these agents not only work with limited efficacy, they also exert certain side effects on their own. Furthermore, none of these agents have demonstrated positive effects on the life expectancy of cancer patients. Finally, a recent report suggests that erythropoietin may actually impair, not improve, survival of cancer patients [Brower, V. (2003), "Erythropoietin may impair, not improve, cancer survival," Nature Med. 9, 1429, and references therein].

Based on these data in the literature, it is clear that there is an unmet need for agents or combinations of agents that can simultaneously enhance the efficacy and tolerability of various forms of cancer therapy including chemotherapy and radiotherapy. Embodiments of the present invention provide selected CC compounds and PALP as well as their combinations that increase the effects of chemotherapy on tumor size, prevent chemotherapy-induced loss of body weight, and extend the survival of experimental animals in some tumor models. These CC compounds and alkaline phosphatase may also have positive effects when combined with other forms of cancer therapy such as radiotherapy and surgery.

Active Compositions

Embodiments of the present invention provide chemically synthesized compounds that contain one or two quaternary ammonium group(s) attached to a non-phospholipid and non-phosphorous heterocyclic hydrophobic moiety to reduce the viability of rapidly proliferating abnormal cells. In this group of compounds, three alkanes, alkenes, alcohols or amines, or their combinations, replace three hydrogen atoms in the ammonium moiety. These compounds were designed to enter the cell interior and interact with the mitochondrial membrane as well as inhibit choline transport and thereby the synthesis of PCho and PtdCho. Since rapidly proliferating cells require proportionally more PtdCho, inhibitors of choline transport are expected to more effectively inhibit the growth of the hyperproliferating abnormal cells, such as psoriatic keratinocytes and malignant cells, than that of normal cells.

A general formula to represent the members of this class of compounds is as follows:

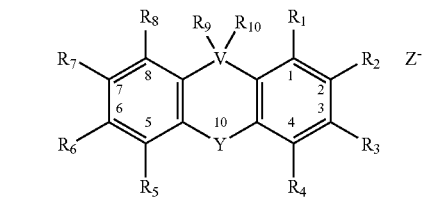

In this formula, $R_1$ and $R_{3-8}$ may be independently chosen from hydrogen or from $C_1$-$C_{26}$ straight, branched or cyclic alkanes or alkenes, aromatic hydrocarbons, alcohols, ethers, aldehydes, ketones, carboxylic acids, amines, amides, nitriles or five- and/or six-membered heterocycle as well as their derivatives.

Further, the variables, $R_9$ and $R_{10}$, considered or taken together may be =O or =CH-L-N$^+$($R_{11}$, $R_{12}$, $R_{13}$) (where -L-N$^+$($R_{11}$, $R_{12}$, $R_{13}$) is defined below). In addition, $R_9$ and $R_{10}$ considered or taken independently may be —OH or -L-N$^+$($R_{11}$, $R_{12}$, $R_{13}$).

The variables, V and Y, may be —S— or —Se—. Alternatively, the sulfur and selenium atoms in the heterocyclic moiety may further be replaced with the carbon, oxygen, or silicon atoms. In yet other embodiments, either V or Y, or both, may be the N atom. In that case the -L-N$^+$($R_{11}$, $R_{12}$, $R_{13}$) group can also be attached to the N atom. For example, in phenoxazine the Y is N, and in that case the -L-N$^+$($R_{11}$, $R_{12}$, $R_{13}$) group can be linked to the N atom. Or in phenazine, both V and Y is N, and the -L-N$^+$($R_{11}$, $R_{12}$, $R_{13}$) group can be linked to both N atoms.

In the general formula, Z$^-$ may be Cl$^-$, Br$^-$ or I$^-$.

Also, in this general formula the variable, $R_2$, may be represented by the following additional formula:

In this additional formula, X may be —CH$_2$—, —OCH$_2$—, —CH$_2$O—, —SCH$_2$— or —CH$_2$S—. Further, L may be $C_1$-$C_4$ straight alkane, alkene, thiol, ether, or amine.

The variables $R_{11}$, $R_{12}$ and $R_{13}$ may be represented by $C_1$-$C_4$ straight alkanes, alkenes, ethers, thiols, amines or alcohols. Preferably, the $R_{11}$, $R_{12}$, and $R_{13}$ groups are represented by methyl, ethyl, allyl, sulfhydryl, ether, amino, or hydroxyl groups or by their combinations. If one $R_{11}$, $R_{12}$ or $R_{13}$ group is an alcohol or an amine, this allows further modification by targeting moieties (see below).

The above described quaternary ammonium-containing compounds may be further altered to contain in alcohol or amine-containing X-L-N$^+$($R_{11}$, $R_{12}$, $R_{13}$) or =CH-L-N$^+$($R_{11}$, $R_{12}$, $R_{13}$) groups a specific targeting moiety to direct the compound to specific tissues. Such targeting molecules may be, for example, specific antibodies (recognizing antigens on the surface of non-healthy cells), folic acid (recognizing highly expressed folate receptor on the surface of certain types of tumor cells), steroids (recognizing the estrogen receptor in breast cancers), fatty acids, or specific peptides, such as transferrin, that can bind to cell surface receptors. These targeting molecules as well as their combination with alcohols or amines are well known to one having ordinary skill in this art.

Using an appropriate heterocyclic compound, such as for example 4,7-phenanthroline or phenazine that has N atoms both in the 9th and 10th positions, L-N$^+$($R_{11}$, $R_{12}$, $R_{13}$) moieties of varying compositions can be attached to both N atoms. For example, in the first L-N$^+$(R$_{11}$, R$_{12}$, R$_{13}$) moiety one of the R$_{11\text{-}13}$ groups may be an alcohol or amine which allows further addition of a targeting group, while in the second L-N$^+$(R$_{11}$, R$_{12}$, R$_{13}$) moiety there would be no alcohol or amine.

In experiments performed in embodiments of the invention, certain compounds described by the general formula were less effective inhibitors of choline transport and cancer cell proliferation. For example, several compounds, including celestine blue, gallocyanine, meldola blue, methylene blue, methylene green, methyl green and pyronin, all containing at least one quaternary nitrogen ion (with two methyl groups) attached via a double bond to a heterocyclic moiety, were ineffective or less effective than, for example, CCDTHT in inducing cancer cell death. Despite these observations, for the purpose of embodiments of the invention, the thioxanthene or thioxanthone moiety may be replaced with any other heterocyclic moiety to which it is feasible to attach at least one quaternary nitrogen group with three substituents that together are capable of inhibiting the transport of external choline into cells and thereby inhibit cell proliferation.

Several subsets of thioxanthene/thioxanthone-based compounds were synthesized in certain embodiments of the invention. Examples of the synthesized compounds include, but are not limited to (i) N,N,N-trialkyl-2-[(9-oxo-9H-thioxanthen-2-yl)methoxy]ethanaminium iodide, ii) N,N,N-trialkyl-2-[(9-oxo-9H-thioxanthen-2-yl)methoxy]propan-1-aminium iodide and iii) N,N,N-trialkyl-3-(9H-thioxanthen-9-ylidene)-propan-1-aminium iodide.

One embodiment of these compounds is N,N-diethyl-N-methyl-2-[(9-oxo-9H-thioxanthen-2-yl)methoxy]-ethanaminium iodide or CCDTHT (or CCompound3), the structure of which is shown along the structure of other CCompounds in Table 1. CCDTHT and all the other CC compounds shown in Table 1, with the exception of CCompound1, have been newly synthesized as reported the first time in this application, and are not available commercially. The synthesis of CCDTHT is described in Example 1. The synthesis of CCompounds 17-20 as well as compounds 23, 25 and 26 are also described in Examples 2-6. While CCDTHT was not always the most effective CC compound in inhibiting the proliferation of various cancer cells in vitro, it was selected for animal experiments based on its relatively low toxicity against normal cells in earlier experiments. However, based on in vitro experiments with breast cancer cells, it is expected that in some tumors, such as estrogen receptor-positive breast cancer, CCompound26 is more effective.

Single treatments with 450 µmole (about 4.6 mg/kg) CCDTHT or daily treatments for 5 consecutive days with 400 µmole of CCDTHT did not cause any significant change in the composition of various blood constituents in mice. Similarly, such treatments did not induce significant pathological alterations in the liver, brain, kidney, heart, spleen, intestine, and lung. However, significant alterations were observed in several tissues, accompanied by the death of 40% of animals by day 30, at the 900 µmole (about 9.2 mg/kg) dose of CCDTHT. Namely, 900 µmole CCDTHT caused mild parenchymal degeneration in the heart, focal hypostasis and chronic bronchopneumonia in the lung, and multifocal degeneration of hepatocytes in the liver. Accordingly, a well-tolerated dose for CCDTHT in mice is 450 µmole/animal (weighing about 25 g) which corresponds to a dose of 4.6 mg/kg. Therapeutically effective concentrations in humans will exert maximal inhibitory effects on the growth of non-healthy tissues without causing significant toxicity in normal healthy tissues.

Parallel toxicological studies also have been performed with 200-500 µmole/animal doses of the commercially available CCompound1. It was similarly well tolerated by the treated mice, although in studies performed in vitro CCDTHT had less inhibitory effects on the proliferation of normal human fibroblasts compared to CCompound1. Since the in vitro studies suggested that in the long-term CCompound1 may develop some toxic side effects, most in vivo studies with mouse cancer models were performed with CCDTHT. CCompound26, which may have an even better toxicity profile based on in vitro experiments with normal cells, was synthesized much later and has not yet been tested in animal experiments.

TABLE 1

A Representative List of CC compounds Used in the Invention.

| Trivial name | Chemical name | Structure |
| --- | --- | --- |
| CCcompound 1 | [3-(3,4-Dimethyl-9-oxo-9H-thioxanthen-2-yloxy)-2-hydroxypropyl]trimethyl-ammonium chloride | 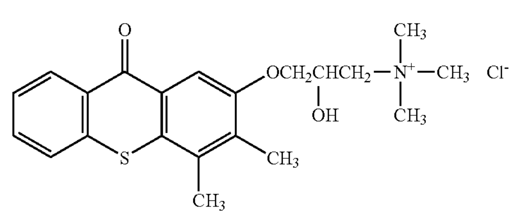 |
| CCcompound 2 | N,N,N-Trimethyl-2-[(9-oxo-9H-thioxanthen-2-yl)methoxy]-ethanaminium iodide | 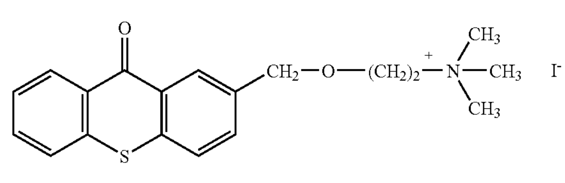 |

TABLE 1-continued

A Representative List of CC compounds Used in the Invention.

| Trivial name | Chemical name | Structure |
| --- | --- | --- |
| CCcompound 3 | N,N-Diethyl-N-methyl-2-[9-oxo-9H-thioxanthen-2-yl)methoxy]-ethanaminium iodide | 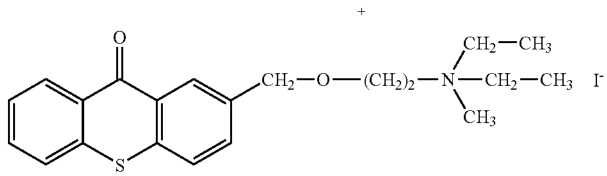 |
| CCcompound 4 | N,N,N-Triethyl-2-[(9-oxo-9H-thioxanthen-2-yl)methoxy]-ethanaminium iodide | 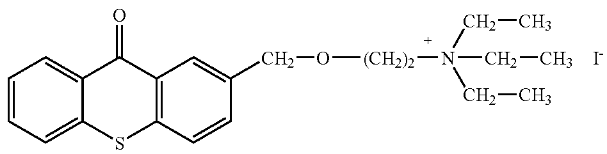 |
| CCcompound 5 | N-Ethyl-N,N-dimethyl-2-[(9-oxo-9H-thioxanthen-2-yl)methoxy]-ethanaminium iodide | 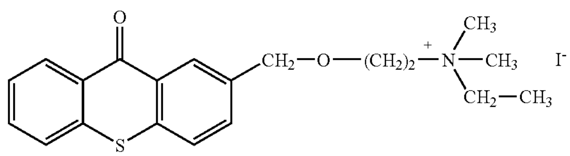 |
| CCcompound 6 | 2-{[2-(Diethylamino)ethoxy]methyl}-9H-thioxanthen-9-one hydrochloride | 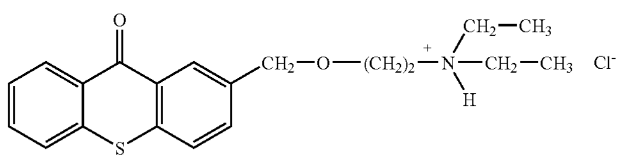 |
| CCcompound 7 | N,N,N-Trimethyl-3-[(9-oxo-9H-thioxanthen-2-yl)methoxy]-propane-1-aminium iodide | 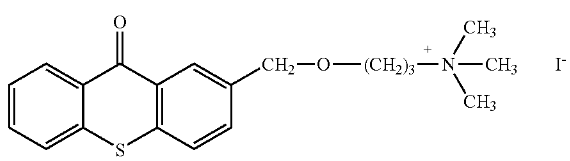 |
| CCcompound 8 | 2-{[3-(Dimethylamino)propoxy]methyl}-9H-thioxanthen-9-one hydrochloride | 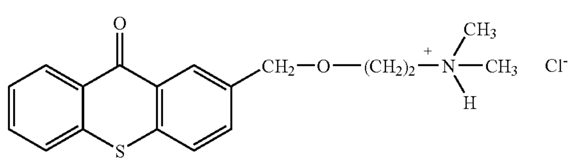 |
| CCcompound 9 | N,N,N-Triethyl-3-[(9-oxo-9H-thioxanthen-2-yl)methoxy]-propane-1-aminium iodide | 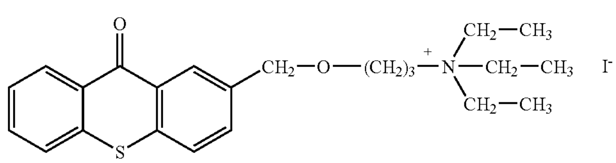 |
| CCcompound 10 | N,N-Diethyl-N-methyl-3-[(9-oxo-9H-thioxanthen-2-yl)methoxy]-propane-1-aminium iodide | 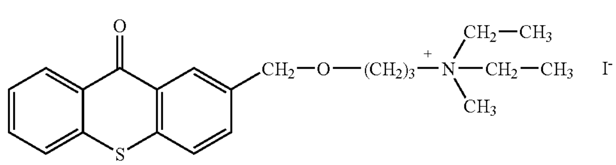 |
| CCcompound 11 | N,N-Dimethyl-N-ethyl-3-[(9-oxo-9H-thioxanthen-2-yl)methoxy]-propane-1-aminium iodide | 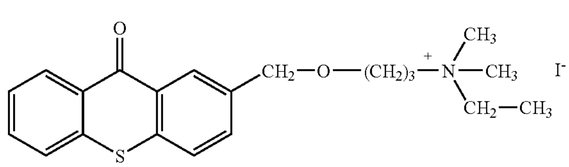 |

TABLE 1-continued

A Representative List of CC compounds Used in the Invention.

| Trivial name | Chemical name | Structure |
| --- | --- | --- |
| CCcompound 12 | 2-{[3-(Diethylamino)propoxy]methyl}-9H-thioxanthen-9-one hydrochloride | 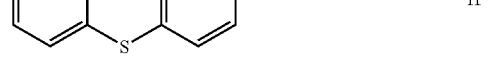 |
| CCcompound 13 | 2-Hydroxy-N,N-dimethyl-N-[(9-oxo-9H-thioxanthen-2-yl)methyl]-ethanaminium bromide | 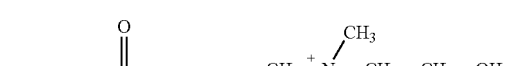 |
| CCcompound 14 | 2-Hydroxy-N,N-Diethyl-N-[(9-oxo-9H-thioxanthen-2-yl)methyl]-ethanaminium bromide | 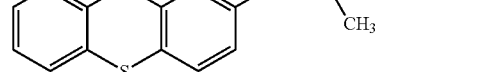 |
| CCcompound 15 | 3-Hydroxy-N,N-dimethyl-N-[(9-oxo-9H-thioxanthen-2-yl)methyl]propane-1-aminium bromide | 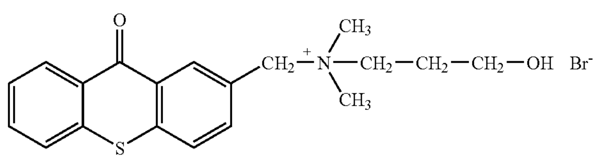 |
| CCcompound 16 | 3-Hydroxy-N,N-diethyl-N-[(9-oxo-9H-thioxanthen-2-yl)methyl]-propane-1-aminium bromide | 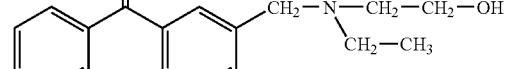 |
| CCcompound 17 | 3-(9-hydroxy-9H-thioxanthen-9-yl)-N,N,N-trimethyl-propane-1-aminium iodide | 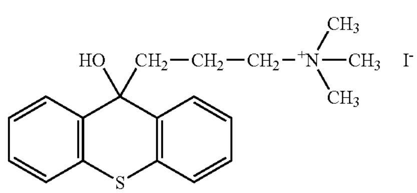 |
| CCcompound 18 | 3-(9-hydroxy-9H-selenoxanthen-9-yl)-N,N,N-trimethyl-propane-1-aminium iodide | 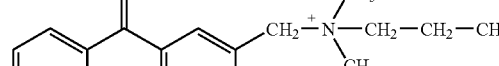 |
| CCcompound 19 | N,N,N-trimethyl-3-(9H-thioxanthen-9-ylidene)-propane-1-aminium iodide | 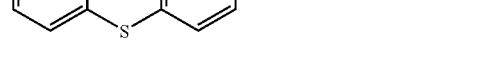 |

TABLE 1-continued

A Representative List of CC compounds Used in the Invention.

| Trivial name | Chemical name | Structure |
| --- | --- | --- |
| CCcompound 20 | N,N,N-trimethyl-3-(9H-selenoxanthen-9-ylidene)-propane-1-aminium iodide | 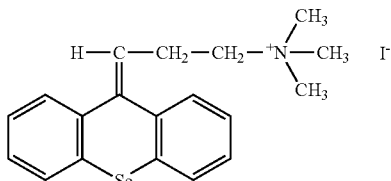 |
| CCcompound 21 | N,N,N-trimethyl-3-(2-methyl-9H-thioxanthen-9-ylidene)-propane-1-aminium iodide | 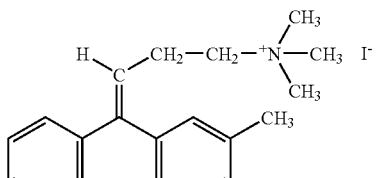 |
| CCcompound 22 | N,N-Dimethyl-N-ethyl-3-(2-methyl-9H-thioxanthen-9-ylidene)-propane-1-aminium iodide | 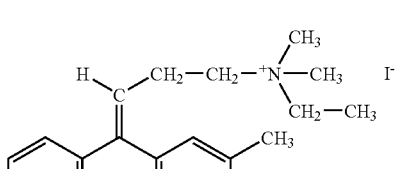 |
| CCcompound 23 | N,N-Diethyl-N-methyl-3-(2-methyl-9H-thioxanthen-9-ylidene)-propane-1-aminium iodide | 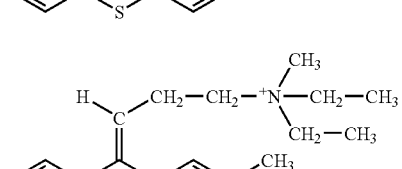 |
| CCcompound 24 | N,N-Dimethyl-N-allyl-3-(2-methyl-9H-thioxanthen-9-ylidene)-propane-1-aminium bromide | 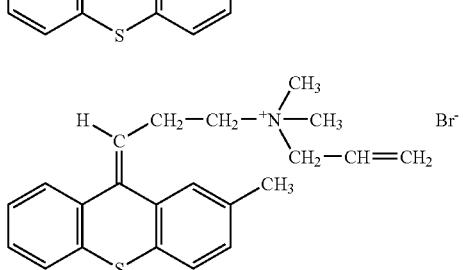 |
| CCcompound 25 | N,N,N-Triethyl-3-(2-methyl-9H-thioxanthen-9-ylidene)-propane-1-aminium iodide | 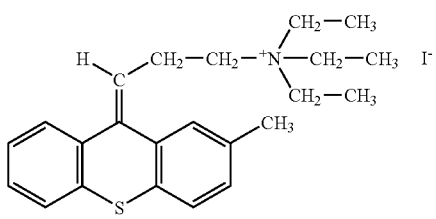 |
| CCcompound 26 | N,N-Diethyl-N-allyl-3-(2-methyl-9H-thioxanthen-9-ylidene)-propane-1-aminium bromide | 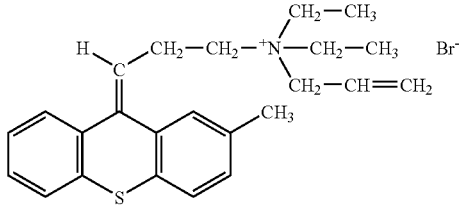 |

The second agent used without or with CC compounds in the methods and compositions in embodiments of the present invention is human placental alkaline phosphatase (PALP), or an active derivative thereof.

As used herein, the term "PALP" and the phrase "human PALP" are used interchangeably to refer to placental alkaline phosphatase. The phrase "active PALP" means the human protein and its glycosylated and non-glycosylated forms as well as peptides derived from these proteins that, when administered with or without CCompounds and/or other chemotherapeutic agents can increase the effectiveness of chemotherapy resulting in decreased tumor size, normalized body weight, and increased life expectancy.

PALP is a member of the alkaline phosphatase group of enzymes that hydrolyze phosphate-containing compounds at alkaline pH. Mature PALP is a dimer of two identical glycosylated subunits. Each subunit has an approximate molecular weight of 66 kDa, as determined by gel electrophoresis. Other members of this phosphatase group include the tissue non-specific (liver/bone/kidney), the intestinal, and PALP-like (germ-cell) alkaline phosphatases.

As mentioned earlier, PALP was found to enhance proliferation and survival of fibroblasts and some other types of healthy cells. Furthermore, it was demonstrated that PALP in its native state exhibiting alkaline phosphatase activity is not required to achieve a beneficial effect on mitogenesis. For example, both digestion of PALP with the protease bromelain and elimination of alkaline phosphatase activity through mutation provided an active derivative [U.S. patent application Ser. No. 10/653,622, filed Sep. 2, 2003 and entitled "Use of Placental Alkaline Phosphatase to Promote Skin Cell Proliferation"; Pub. No. US2005/0048046 A1, Pub. Date, Mar. 3, 2005]. Consequently, one who is skilled in the art may synthesize or develop an active derivative that is a smaller fragment of a PALP amino acid sequence and demonstrates efficacy similar to that of native PALP. By way of example, modification of a PALP amino acid sequence or a sequence of smaller PALP peptides by exchanging amino acids at critical sites to yield an active derivative may improve the beneficial effects of PALP in combination with the other proteins disclosed herein. Likewise, chemical or enzymatic changes in the level and position of glycosylation may maintain or enhance the effects of PALP or its derivatives. In the practice of embodiments of the present invention, it is envisioned that modified PALP, smaller PALP-derived peptides, or modified PALP-derived peptides may be similarly effective or even more effective than the native PALP enzyme, and are each considered to be active derivatives. Likewise, PALP molecules isolated from placenta tissue or produced in recombinant form are considered to be similarly effective.

While the stimulatory effects of PALP on the proliferation of normal cells may not require its enzyme activity, the effects of PALP on the survival and proliferation of cells in vivo may be, at least in part, the result of an indirect action. For example, PALP may activate immune cells via its phosphatase activity resulting in the release of cytokines and growth factors that then may partly mediate the effects of PALP on normal cells. Similarly, the major anti-cancer effects (for example, decrease of tumor size) of PALP may require phosphatase activity. Another possibility is that while phosphatase activity may not be required for either effect, the structures of various alkaline phosphatases are sufficiently similar to cause similar effects on cell survival and proliferation. For example, it is known that all alkaline phosphatases interact in the plasma membrane with a common binding or anchoring site, called GPI anchor [J. L. Millan and W. H. Fishman (1995), "Biology of human alkaline phosphatases with special reference to cancer," Critical Reviews in Clinical Sciences 32, 1-39]. Accordingly, each human alkaline phosphatase enzyme may at least partially mimic the effects of PALP both on normal as well as cancer and other abnormally growing cells.

Human PALP in solid form is available commercially from Sigma-Aldrich (St. Louis, Mo.), for example (Sigma catalog number P3895; CAS Registry Number 9001-78-9). Another commercial source of human PALP is Calbiochem (San Diego, Calif.; catalog number 524604).

Human PALP, and particularly a smaller molecular mass active derivative, may also be obtained by chemical synthesis using conventional methods. For example, solid-phase synthesis techniques may be used to obtain PALP or an active derivative.

Recombinant methods to obtain quantities of PALP (and active derivative) are also suitable. Since the cDNA of PALP is available, recombinant protein can be produced by one of the many existing conventional methods for recombinant protein expression. PALP has been cloned and overexpressed in a mammalian cell line [Kozlenkov, A., Manes, T., Hoylaerts, M. F. and Millan, J. L. (2002), Function assignment to conserved residues in mammalian alkaline phosphatases," J. Biol. Chem. 277, 22992-22999; J. L. Millan and W. H. Fishman (1995), "Biology of human alkaline phosphatases with special reference to cancer," Critical Reviews in Clinical Sciences 32, 1-39]. Production of recombinant PALP by both bacteria [Beck, R. and Burtscher, H. (1994), "Expression of human placental alkaline phosphatase in *Escherichia coli*," Protein Expression and Purification 5, 192-197] and yeast [Heimo, H., Palmu, K. and Suominen, I. (1998), Human placenta alkaline phosphatase: Expression in *Pichia pastoris*, purification and characterization of the enzyme," Protein Expression and Purification 12, 85-92] have also been reported.

Bacterial expression yields non-glycosylated PALP. So far there is no evidence that the anti-cancer effects of native glycosylated PALP and bacteria-produced PALP would be significantly different. Thus, in the methods of embodiments of the present invention native glycosylated PALP and its active derivatives as well as non-glycosylated PALP and its active derivatives may be used interchangeably.

A PALP preparation that is commercially available contains impurities. Impure PALP preparations can be used as starting material to obtain homogeneous PALP by successive chromatographic steps, as described in detail in Example 1. Impure PALP preparations may also be used in formulating the compositions for use in the practice of embodiments of the present invention, so long as the given composition comprises therapeutically effective amount of PALP, and impurities are not toxic and do not interfere with the beneficial effects of the components.

A preparation containing human PALP may also be obtained by extraction from placental tissue. Human placenta synthesizes the enzyme during pregnancy, so that toward the end of the third term, the level of PALP in the placenta tissue and the maternal/fetal blood becomes very high. By way of example, a preparation may be obtained by butanol extraction of homogenized placenta. Other methods of extraction from placental tissue are also suitable.

Raw placental extracts that are not further enriched in PALP by using physical concentration methods cannot be expected to have physiological effects similar to those observed for the preparation of sufficiently enriched or purified or homogenous PALP, for at least two reasons. First, the relative concentration of PALP in an extract will be too low to expect a readily detectable anti-cancer effect. Second, raw placental extracts contain not only many different proteins but also other kinds of compounds, such as many lipids, proteolipids, carbohydrates, metals, vitamins, and the like that may cause unexpected side effects. An additional consideration is that only sufficiently highly purified PALP can be introduced into the clinical practice to ensure the standard quality of the preparations and to exclude the health risks caused by unidentified contaminants.

Therefore, if placenta-derived PALP preparation is to be used in the practice of embodiments of the present invention, a raw extract should be treated to enrich the concentration of PALP and obtain a substantially purified or highly purified preparation. A highly purified preparation will have a much higher concentration of the active component than found in a raw tissue extract. A highly purified PALP preparation does not contain detectable amounts of contaminants or contains such a minimum amount of known contaminants that the benefits of using the preparation far out-weight the accompanying potential risks. The term "substantially purified" is used herein to encompass compositions that are obtained from a starting material by one or more purification steps (such as solvent extraction, column separation, chromatographic separation, etc.) that enrich the concentration of PALP, relative to the starting material, to an extent that PALP is the dominating component, and the remaining components do not pose any significant health risk and do not reduce the beneficial effects of PALP. The term "substantially purified" should not be construed to connote absolute purity.

The stimulatory effect of PALP on fibroblast proliferation in vitro is enhanced by pre-heating it at 65-75° C. for 30 minutes [Q.-B. She, J. J. Mukherjee, J.-S. Huang, K. S. Crilly, and Z. Kiss (2000), "Growth factor-like effects of placental alkaline phosphatase in human fetus and mouse embryo fibroblasts," FEBS Letters, 468, 163-167]. Although not tested yet, it is reasonable to expect that pre-heating of PALP at 65-75° C. prior to its use may also enhance some aspects of its anti-cancer effects relating to the protection of normal tissues. Thus, a step of heat-activation may be included during the final preparation of PALP for injection.

The stimulatory effect of PALP on fibroblast proliferation in vitro is also enhanced by adding calcium and zinc to the medium [Q.-B. She, J. J. Mukherjee, J.-S. Huang, K. S. Crilly, and Z. Kiss (2000), "Growth factor-like effects of placental alkaline phosphatase in human fetus and mouse embryo fibroblasts," FEBS Letters, 468, 163-167]. Accordingly, the final preparation of PALP for injection may include 1-3 mM of a calcium-containing compound (for example, calcium chloride) and/or 1-50 µM of a zinc containing compound (for example, zinc chloride or zinc sulfate).

Substantially purified preparations of bone-specific, tissue non-specific, and PALP-like (germ) alkaline phosphatase enzymes are all available commercially (for example, from Sigma-Aldrich). Appropriate purification methods are known for their isolation from human blood, liver, and other organs. Also, recombinant forms of each of these alkaline phosphatases have already been produced.

Methods of Use

CC Compounds.

CCDTHT and other CC compounds may be used for the treatment of various skin proliferative diseases, including psoriasis and skin cancer, and other proliferative diseases and cancers located in other organs. In one embodiment suitable for the treatment of proliferative skin diseases such as, for example, psoriasis and skin cancer, the application is topical where the CC compound is mixed in a cream, rinse, gel, ointment, and the like. In some embodiments, the creams, ointments, and the like containing a CC compound can be delivered by dressings, bandages, or other similar coverings capable of releasing the therapeutic amount of these compounds. Such dressings can be directly placed on the hyperproliferative skin area. Oral application is another method of delivering a CC compound in a therapeutically effective amount. In one embodiment of the invention, the CC compound is in the form of a tablet, gel capsule, a liquid, or the like. In each case, the CC compound is mixed with one or more carriers chosen by one having ordinary skill in the art to best suit the goal of treatment. In yet another embodiment, the selected CC compound is mixed in a liquid biocompatible carrier, such as physiological saline (0.9% NaCl), and injected via one of the systemic routes such as, for example, intravenous, intraarterial, intraperitoneal, subcutaneous, intramuscular, intracranial, intraportal, or intradermal. Yet another mode of application is direct injection of CC compound-containing solution into the aberrant tissue such as a tumor tissue.

The various application methods can be mixed or used alternatively. For example, in case of proliferative skin diseases, simultaneous topical and systemic treatments with CCDTHT are expected to exert greater effects than either the topical or systemic application alone. As a rule, for the treatment of proliferative skin diseases, combined topical and systemic or oral applications are recommended. For the treatment of proliferative diseases of the internal organs such as solid and blood cancers, either oral or systemic application of CC compounds is the most suitable.

The therapeutic amount of the selected CC compound that is necessary to be delivered depends on the application method, the location of the targeted organ, the stage of the disease, the combination of its use with other treatments, the age of the patient, the goal of the treatment, and other factors. The health care provider who possesses all the required information determines the required therapeutic amount. By an example, in case of topical application the concentration of the CC compound in a composition will be at least about 0.01 wt.-%, and more suitably, between about 0.1 and about 2 wt.-%. In one embodiment, the composition comprises about 0.2 to about 1.0 wt.-% of the active component. In case of applications by injection, one dose will preferably contain between about 10 to about 2,500 mg CC compound per $m^2$ body surface. In a suitable embodiment, the injectable composition contains 100 to about 600 mg CC compound per $m^2$ body surface.

The CC compound can be administered via one of the application routes for a suitable amount of time period. The length of a suitable time period, which may be 1 week, 1 month, or as many months as necessary, is individually determined by the care provider and depends on the severity of the situation and other factors. The care provider also determines the frequency of the treatments. In some embodiments, the CC compound may be delivered three-times every 24 hours; in other cases, once per day, three-times a week, or once a week.

The CC compound-containing compositions for topical treatment may include various additives or enhancers. The criterion for using an additive/enhancer is that it increases, or at least does not decrease, the effectiveness of the active components in achieving the desired beneficial effect. Additives or enhancers in compositions for topical applications may include various ingredients, for example, preservatives (such as parabens, alcohols, phenols, essential oils, and the like), buffers, antioxidants (such as vitamin E, flavons, flavonoids, resveratrol), antimicrobials, vitamins, moisture-control agents (such as glycerine, propylene glycol, and the like), analgesics, anesthetics, anti-psoriatic agents, and anticancer agents. Other additives may include, for example, emulsion stabilizers, preservatives, waterproofing agents, viscosity modifying agents, and the like.

For skin applications, the CC compound-containing products can also include pharmaceutically acceptable carriers or vesicles. Preferably, the carriers are non-toxic. A pharmaceutically acceptable carrier does not elicit an adverse physiological reaction in normal skin upon administration and is one in which the CC compound is sufficiently soluble to deliver therapeutically effective doses. As used herein, "pharmaceutical" is understood to encompass both human and animal pharmaceuticals. Carriers and vehicles can be included in the CC compound products to obtain an appropriate consistency, for example, gels, lotions, cream, rinse, and the like. These products are suitable as topical compositions to control proliferation of non-healthy skin cells.

Suitable carriers generally include, for example, water, acetone, ethanol, ethylene glycol, propylene glycol, butane-1,3-diol, isopropyl myristate, isopropyl palmitate, mineral oil, mixtures thereof, and the like. Buffered solutions can also serve as carriers.

In some embodiments, the topical composition is a gel. The gel may include as a carrier methylcellulose, sepharose, agar, vaseline or petrolatum, agarose, gelatin, dextran, dextran-polyethylene, polyhydroxyethylmethacrylate, hydrophilic cellulose polymer, polyethylene glycol, polyvinylpyrrolidine, amylose, polyethyleneoxide, calcium alginate or combination thereof. By way of example, the selected sterilized (filtered) CC compound can be incorporated into sterile 3% by weight methyl cellulose gel, 1% by weight agarose gel, 4% by weight gelatin gel, or 1 to 3% by weight calcium alginate. Gels of more complex compositions can be formulated. One having ordinary skill in the art will recognize how to vary these components to obtain sustained release of CC compounds.

In some embodiments, the carrier includes vaselinum flavum (yellow petrolatum), vaselinum album (white petrolatum), or vaselinum cholesterinatum. Commercially available vaselinum cholesterinatum consists of about 1.5 wt.-% cholesterol, about 5.0 wt.-% cerae lanae, and about 93.5 wt.-% vaselinum flavum.

The CC compound-containing compositions can be stored at room temperature for at least one year and at 4° C. for several years under aseptic conditions.

Embodiments of the present invention also provide CC compound-containing compositions suitable for transdermal administration. Such compositions are applied directly to the skin or incorporated into a protective carrier such as a transdermal device, i.e. a patch. Examples of suitable creams, ointments, or the like, can be found, for example, in the Physician's Desk Reference. Examples of suitable transdermal devices are described in, for example, U.S. Pat. No. 4,818,540 to Chien et al. entitled "Transdermal Fertility Control System and Process", incorporated herein by reference.

The CC compound-containing compositions can be made using a number of suitable techniques. In some embodiments, the CC compound and a carrier are mixed together within a commercial mixer to form a solution, a suspension, or the like. Various equipments are also available to manufacture liposomal preparations (which provides for controlled, sustained release of the CC compound). In pharmaceutical composition embodiments, methodologies for the formulation are well known, and can be found, for example, in Remington's Pharmaceutical Sciences, Eighteenth Edition, A. R. Gennaro, Ed., Mack Publishing Co. Easton, Pa. 1990, incorporated hereby by reference.

To treat hyperproliferative internal tissues, such as cancer, embodiments of the invention include CC compound in the form of a tablet or a gel-like shaped composition suitable for oral consumption or application through the rectum. In addition to CCDTHT, the tablet or gel may contain any component that is presently used in the pharmaceutical practice to ensure firmness, stability, solubility and appropriate taste. Any component of the tablet will be chemically inert; i.e., it will not participate in a chemical reaction with the CC compound or the other additives. The tablet or gel may contain, in addition to the active component and tablet-forming components, other biologically active compounds such as, for example, an anticancer agent(s) or agents that promote(s) the actions of the CC compound. Without aiming to present a full list, the agents increasing the effects of CC compound, for example, on cancer tissue, may include ethacrynic acid (ETA) and similar agents (L-buthionine-S,R-sulfoximine, diethylmaleate, 2-cyclohexene-1-one, 1-chloro-2,4-dinitrobenzene) which decrease the cellular level of glutathione, zinc, or cadmium at concentrations which decrease the proliferation of non-healthy cells but are non-toxic to normal cells, pyrrolidinedithiocarbamate and any other chelator which can bind and carry vitally important metal ions such as, for example, zinc, copper, or iron, any agent that can reverse multidrug or other forms of drug resistance, or any other anti-proliferation/anticancer agent or drug which acts additively or synergistically with the CC compound and is suitable to mix with a CC compound to make a tablet, a gel capsule and the like for oral delivery.

Appropriate solutions of the selected CC compound, which may include other anti-cancer (anti-proliferation) drugs or additives, can also be applied via other routes including intravenous, intramuscular, intraperitoneal, intradermal, intraarterial, intracranial, intraportal, and subcutaneous injections or aerosol. Yet another mode of application is direct injection into the aberrant tissue such as a tumor tissue. For all injection methods, the CC compound can be dissolved in any appropriately accepted solvent or medium which provides good solubility and which is physiologically compatible. One generally accepted medium is physiological saline (0.9% NaCl). The compound, CCDTHT, and most of the other CC compounds including CCompound26, are sufficiently soluble in water for injection.

For both topical applications on the skin and injection treatments of internal non-healthy tissues, the CC compound-containing compositions may be used as the sole method of medication, or they may be used in combination with other treatments. For example, it is envisioned that in the case of psoriasis, the CC compound-containing composition may be used either alone or in combination with available anti-psoriasis agents acting, in most cases, by suppressing the actions of specific immune cells. The same may be true for some cancers, such as ovarian cancer, where the selected CC compound may be sufficiently effective alone (based on in vitro data); however, it could become even more effective when cisplatin or other anti-cancer agents are used simultaneously. Similarly, in the elderly, who may not tolerate highly toxic chemotherapy, treatments with the CC compound alone may be more beneficial than strongly cytotoxic drugs to prolong life without causing major side effects. However, in most cases it is recommended that the selected CC compound be used together with an anti-proliferation agent, such as anti-cancer agent, to enhance the efficacy and decrease the toxicity of the latter agents.

In case of certain cancers CC compound-containing compositions may be used between two series of chemotherapy (which are usually 2-3 weeks apart), to allow patients to recover from the side effects of chemotherapy and to ensure at least partial suppression of tumor growth between the chemotherapeutic treatments. However, the CC compound-containing compositions may also be used simultaneously with other chemotherapeutic agents, allowing the latter agents to be used at lower concentrations with less toxic side effects. The sequence of treatments with chemotherapeutic agents and CC compound-based formulas, the length of each treatment, and the dosing of CC compound and various anticancer agents will be determined, based on previous experience, individually by the health care provider.

CC compound-containing compositions may be used in combination or alternatively with anti-proliferation treatments other than chemotherapy, such as radiation and surgery, for example. In one regimen, the CC compound-containing cream may be used after radiation and/or surgical procedures as an after treatment to prevent local recurrence of skin cancer. In another regimen, CC compound-containing solution is applied by one of the injection methods after surgical removal of tumor from an internal organ or after completing a course of chemotherapy or radiotherapy to prevent recurrence of the primary tumor or development of secondary tumors.

It is now generally accepted that most, if not all, tumors are heterogeneous due to their multiclonal origin. This means that the nature and level of aberrations are somewhat or significantly different in different sub-populations of the tumor-forming cells. In practical terms, this means that subsets of cells in the same tumor may not respond similarly to the same treatment. In the present invention, different CC compounds are shown to exert in some cases different effects against different cancer cell types. For example, different CC compounds inhibit the proliferation of the MEL-24 and MEL-28 human melanoma cells. Therefore, in one embodiment of treating human or mammalian tumors two or more CC compounds may be used in the compositions used for oral, local, or systemic applications. Such compositions then can be used in combination with other anti-proliferation treatments such as chemotherapy, radiation, surgery, or suppression of the immune system.

Alkaline Phosphatase.

The model alkaline phosphatase used as an anticancer agent in embodiments of the invention is the placental form of alkaline phosphatase (PALP) produced by the placenta during pregnancy. However, all alkaline phosphatases commonly express an alkaline phosphatase enzyme activity that may play a role in the PALP's anticancer effects. Therefore, other alkaline phosphatase enzymes may mimic, at least in part, the anticancer effects of PALP.

The anticancer effect of PALP has three components; i.e., it (a) alone decreases the size of certain tumors and also enhances the similar effects of anti-cancer agents, including CC compounds, (b) prevents, partially or fully, the decrease in body weight induced by chemotherapy, and (c) increases survival time in certain tumor models. For the treatment of most cancers with an alkaline phosphatase one of the systemic application routes is recommended.

Therapeutically effective amounts of sufficiently highly purified or homogeneous PALP or another alkaline phosphatase may be used as the active component in the compositions described herein. Alternatively, preparations containing synthetic protein or its active derivative, or a recombinant form of alkaline phosphatase or its active derivative, may be employed as the active component. The term "active" means that the preparation of intact alkaline phosphatase, or a fragment of it, exerts at least one of the above listed three anticancer effects. The term "therapeutically effective amount" in this specification indicates a dosage that is effective in exerting at least one of the above three anticancer effects.

A composition comprising the active protein component may be administered by one of the injection methods including intradermal, subcutaneous, intravenous, intraperitoneal, intraarterial, intracranial, and intramuscular applications. The injectable form of the composition is comprised of a therapeutically effective amount of PALP or another alkaline phosphatase or an active derivative thereof.

For injection of a composition comprising the active alkaline phosphatase component, the carrier can be any physiologically acceptable carrier that does not cause an undesirable physiological effect and is capable of ensuring proper distribution of the active components in the treated tissue. The active components are dissolved or dispersed in the physiologically acceptable carrier. Examples of carriers include physiological saline and phosphate-buffered saline. Alternatively, the active alkaline phosphatase component may be enclosed in liposomes such as immunoliposomes, or other delivery systems or formulations that are known in the art may be employed. By way of example, the active protein component can be readily dissolved in physiological saline (0.9% NaCl), or in any other physiologically competent carrier, to yield a solution for injection.

An injectable composition may be prepared by dissolving or dispersing a suitable preparation of the active protein component in the carrier using conventional methods. As examples only, one embodiment of the invention includes PALP in a 0.9% physiological salt solution to yield a total protein concentration of 10 mg/ml. Another embodiment includes PALP in a 0.9% physiological salt solution to yield a total protein concentration of 200 mg/ml.

The injectable composition may be modified by any number of additives and enhancers, as listed above for the topical application, that may be dissolved or suspended in the composition and that are expected to promote the anticancer effects of the alkaline phosphatase component or diminish any potential side effect.

In one embodiment of the method, the mode of injection is selected from intradermal, intravenous, subcutaneous, intramuscular, intraarterial, intracranial, intraportal and intraperitoneal. The mode of injection is selected to provide either local delivery to some tumors such as liver tumor (intraarterial), or systemic delivery to other cancers via the blood supply (such as intravenous, intraperitoneal and subcutaneous applications).

A common way to express a suitable dosage for systemic administration is grams of the active agent(s) per square meter of body surface area for the subject. Those having ordinary skill in the art are familiar with the formulas used for estimating a human subject's body surface area, based on the human's height (in cm) and mass (in kg).

In case of intravenous, intraarterial, intramuscular, intraperitoneal, intraportal, intracranial or subcutaneous application, the subject may be administered a total of about 0.02 to 2.5-g PALP per $m^2$ body surface once daily. In another embodiment, a subject may be administered by intravenous, intraarterial, intramuscular, intracranial, intraperitoneal, intraportal, or subcutaneous application a total of about 0.02 to 2.5-g PALP per $m^2$ body surface twice or three times weekly. Alternatively, the subject may be administered a total of about 0.02 to 2.5-g PALP per $m^2$ body surface once a week or biweekly by intravenous, intraarterial, intramuscular, intracranial, intraperitoneal, intraportal, or subcutaneous application. Since the half-life time of PALP is relatively long (5-6 days), in one embodiment of the invention, the protein is applied twice a week or once a week. Again, concerning the effective tolerable dose, an important consideration is whether alkaline phosphatase is used alone or used as part of a more complex regimen involving other anticancer agents as well. For example, if the subject is simultaneously or alternatively treated with both alkaline phosphatase and another therapy, the effective tolerated amount of the former may be less compared to a regimen when the subject is treated with alkaline phosphatase alone.

Use of CC Compound and PALP in Combination.

In various tumor models, the CC compound, CCDTHT (CCompound3), and PALP commonly reduced tumor size, enhanced the effects of chemotherapeutic agents on tumor size, decreased or fully prevented weight loss induced by chemotherapeutic agents, and increased survival. In some cases, as demonstrated under "Examples", the combined effects of CCDTHT and PALP were greater than their individual effects. These findings indicate that there are cases when using a selected CC compound and alkaline phosphatase in combination for the treatment of animal or human tumors will exert greater anti-tumor effects than using them alone. The same is likely to be true for other proliferative diseases as well.

The combined treatment with CC compound and alkaline phosphatase may occur in the absence or presence of other treatments performed simultaneously or alternatively. The combined treatment with CC compound and alkaline phosphatase may also occur prior to or after the other therapies. For example, prior treatment with relatively non-toxic CC compound and PALP could serve to shrink the tumor to a more manageable size for the subsequent surgery and/or radiation. The combined treatment with CC compound and PALP may also be performed as an after treatment following surgical removal and/or radiation treatment of a tumor to reduce local or remote (metastasis) recurrence.

Since CCDTHT and PALP act via independent mechanisms and therefore do not interfere with each other's actions, both agents may be used at the same therapeutically effective doses as recommended when used individually. The same is true for the regimens; similar regimens developed for the individual use of CC compound and alkaline phosphatase may be employed when they are used in combination.

For applications via injection, the injectable preparation may occasionally contain both the CC compound and alkaline phosphatase. However, in this latter case separate application of the CC compound and alkaline phosphatase is more likely because the former requires more frequent applications than the latter. The CC compound-containing injectable preparation may also contain other anticancer agent(s), or the latter may be administered separately.

In addition to injection methods, CC compounds may also be administered orally or topically, independent of the injected alkaline phosphatase.

For the treatment of most cancers, a preferred regimen includes periodical injection or oral administration of an established chemotherapeutic agent accompanied by daily oral administration of CC compound and once or twice a week injection of PALP. Again, this treatment may be combined with surgery and/or radiation, or by any other therapy, either prior to or after the primary therapy.

Example 1

Synthesis of N,N-diethyl-N-methyl-2-[(9-oxo-9H-thioxanthen-2-yl)methoxy]-ethanaminium iodide (CCompound3 or CCDTHT)

This product has been chemically synthesized via the following intermediates:
2-[(4-methylphenyl)thio]-benzoic acid→2-methyl-9H-thioxanthen-9-one→2-(bromomethyl)-9H-thioxanthen-9-one)→2-{[2-diethylamino)ethoxy]methyl}-9H-thioxanthen-9-one→N,N-diethyl-N-methyl-2-[(9-oxo-9H-thioxanthen-2-yl)methoxy]-ethanaminium iodide.

Synthesis of 2-[(4-methylphenyl)thio]-benzoic acid (intermediate 1): 2'-iodo benzoic acid (19.84 g) and p-thiocresol (9.92 g) were dissolved in 120 ml of dimethylformamide; this was followed by the addition of 0.5 g of copper powder, 0.5 g of Cleland's reagent (threo-1-1,4 dimercapto-2,3-butanediol) and 29.52 g of hot $K_2CO_3$. The mixture was heated, refluxed (in an oil bath) with continuous vigorous mixing, and cooled to room temperature. Then the mixture was filtered, and the solid fraction was washed three-times with dimethylformamide. The solid fraction was removed, and the combined filtrate was evaporated (using a Rotadest equipment). The resulting solid fraction was dissolved in water, filtered, placed on ice, and pH adjusted to 1.0 with $H_2SO_4$. The resulting white precipitate was filtered and washed with water until the pH reached 7.0. The efficacy of this reaction is about 80%. The melting point of intermediate 1 is 218-219° C.

Synthesis of 2-methyl-9H-thioxanthen-9-one (intermediate 2): Intermediate 1 (17.0 g) and polyphosphoric acid (110 g) were mixed and then heated to ~150° C. with vigorous mixing for 5 hours. After cooling the mixture to room temperature, ice-cold water was added to it. The mixture was extracted three times with 150 ml of ethylacetate. The combined organic phases were first washed three times with 150 ml of 5% $Na_2CO_3$, then once with water (150 ml), and once with saturated NaCl (150 ml), followed by drying the washed organic phase over water-free solid $Na_2SO_4$. After removing the solvent, the yellow material was re-crystallized from ethanol. The efficacy of this reaction is ~65%. The melting point of intermediate 2 is ~123.50° C.

2-(bromomethyl)-9H-thioxanthen-9-one) (intermediate 3): Intermediate 2 (20.8 g), 1,3'-dibromo-5,5'-dimethylhydantoin (13.5 g) and benzoylperoxide (4.4 g) were suspended in 800 ml of absolute $CCl_4$ (carbon tetrachloride), and then the suspension was refluxed for 20 hours with continuous and rigorous mixing. The mixture was cooled to 10° C. and filtered. The remaining solid material was washed three times with 100 ml water (~75° C.) and then re-crystallized from hot acetone. The solid material was washed with cold acetone. The efficacy of this reaction is 51%. The melting point of intermediate 3 is 196-197° C.

2-{[2-diethylamino)ethoxy]methyl}-9H-thioxanthen-9-one (intermediate 4): 2'-diethylaminoethanol (1.17 g) was dissolved in 50 ml of absolute xylol; then during constant vigorous mixing and warming to 35-40° C. 0.24 g of solid sodium was added in small portions followed by mixing and warming of the mixture for one hour. Intermediate 3 (1.5 g) was added to the mixture in small portions, and the whole mixture was mildly refluxed for 56 hours. The solid material was removed by filtering the mixture. The organic phase was washed four times with 150 ml water. Then, the water was removed by filtration through solid water-free $Na_2SO_4$. After distillation (to remove xylol), the resulting oily, yellow-brown material was not yet pure as determined by thin layer chromatography (Kiesel gel) using benzol:ethanol:water (50:

15:1.5, v/v) as solvent. The mixture was fully purified through the following steps. The mixture was first dissolved in an $(CH_3)_2CO$ (acetone)/absolute ethanol (1:1, by volume) mixture followed by the addition of concentrated HCl until the solid material (HCl salt) was formed. The solid precipitate was washed with cold acetone. The HCl salt of intermediate 4 was dissolved in ethanol:water (10:90, v/v), and the solution was made basic (pH 14) by the addition of solid $Na_2CO_3$. The oily material was extracted with ethylacetate and then dried over solid $Na_2SO_4$. Intermediate 4 is 99-100% pure as determined by $^1$H-NMR and thin layer chromatography. The yield of intermediate 4 is ~55%.

Synthesis of N,N-diethyl-N-methyl-2-[(9-oxo-9H-thioxanthen-2-yl)methoxy]-ethanaminium iodide (CCompound3 or CCDTHT): Intermediate 4 (1.0 g) was dissolved in 5 ml of absolute $(CH_3)_2CO$ (acetone) followed by the addition (at room temperature) of methyl iodide (1 ml). Within 1-2 minutes, a white solid material (CCDTHT) was formed. After keeping the mixture at 4° C. overnight, the solid material was filtered and was washed twice with 100 ml of $(CH_3)_2CO$. CCDTHT is a light-yellow crystallized material. No contaminant can be seen by NMR or thin layer chromatography (TLC; benzol:ethanol:water=50:15:1.5, by volume as solvent) which was reasonable to expect because intermediate 4 was already ~99-100% pure. Also, the precursor and the final product (CCDTHT; Rf=0.35) are physically well separated by TLC, and in the last reaction only one product, i.e. CCDTHT, can be formed. The melting point of CCDTHT is ~225° C.

Example 2

Synthesis of CCompound17, N,N,N-trimethyl-3-(9-hydroxy-9H-thioxanthen-9-yl)-propane-1-aminium iodide Thioxanthone (2.76 g, 13 mmol) was dissolved in 40 ml tetrahydrofuran. The thioxanthone solution was added dropwise, during intensive mixing, to a solution containing 27 mmol of Grignard reagent (made by reacting magnesium first with dibromidemethane and then with dimethylaminopropil chloride by a method well known in the art), 50 ml of diethylether and 50 ml of tetrahydrofuran. The mixture was refluxed for 2.5 hours followed by constant mixing at room temperature for 16 hours. Then, the mixture was added to 200 ml of ice-cold saturated ammonium chloride and the solution was extracted 3-times with 100 ml of ethylacetate. After drying the organic phase over water-free sodium sulfate, the solvent was removed by distillation. The resulting yellow product ($C_{18}H_{21}NOS$) was first re-crystallized from an ethanol/acetone mixture, then re-dissolved (0.6-g) in 10 ml of absolute acetone+2 ml methyl iodide. The mixture was first kept for 24 hours at room temperature and then for 2 days at 4° C. in a closed glass tube (no contact with air). Then, the precipitated crystals were filtered and washed with absolute acetone. The final product ($C_{19}H_{24}JNOS$; Mw+441.385) was dried under vacuum in the presence of $P_2O_5$.

Example 3

Synthesis of CCompound18, 3-(9-hydroxy-9H-selenoxanthen-9-yl)-N,N,N-trimethylpropane-1-aminium iodide In the first step, selenoxanthen-9-one was made by well known conventional steps involving the synthesis of 2-carbonyl selenodiphenol by reacting selenophenol with iodobenzoic acid followed by ring closure in the presence of concentrated $H_2SO_4$. The synthetic steps were then performed as described for the synthesis of CCompound17 in Example 2, except that thioxanthone was replaced with selenoxanthen-8-one.

Example 4

Synthesis of CCompound19, N,N,N-trimethyl-3-(9H-thioxanthen-9-ylidene)-propane-1-aminium iodide CCompound17 was dissolved in a mixture of 35 ml distilled water and 3 ml of concentrated $H_2SO_4$ followed by reflux of the solution for 24 hours. Then, the solution was diluted with 20% (w/v) potassium hydroxide until the pH reached a value between 11 to 12. The resultant white emulsion was extracted 3-times with 100 ml of ethyl acetate. This was followed by washing the organic phase with water until the pH become neutral and drying the organic phase over water-free sodium sulfate. After distillation under vacuum, the product was a light brown oily material that was further enriched in the form of HCL salt. The oily material was dissolved in 20 ml of absolute acetone to which a mixture of ethanol and HCl (ethanol saturated with HCl) was added until crystal formation was induced. Then, the precipitated crystals ($C_{18}H_{20}ClNS$) were filtered, washed with acetone, and dried at room temperature. The crystals were dissolved in water followed by the addition of 50% potassium hydroxide until pH 11 was reached. The precipitate ($C_{18}H_{19}NS$) was filtered, washed with acetone and dried. This basic compound ($C_{18}H_{19}NS$) was dissolved in 10 ml of absolute acetone followed by the addition of 1.2 ml of methyl iodide to the mixture. The crystals that are almost immediately formed at room temperature were kept at 4° C. for 24 hours and then filtered. The precipitate was washed with acetone and dried at room temperature. The molecular weight of the final product ($C_{19}H_{22}JNS$) was 423.

Example 5

The synthesis of CCompound20, N,N,N-trimethyl-3-(9H-selenoxanthen-9-ylidene)-propane-1-aminium iodide The synthesis of this compound was performed similar to that of CCompound19 as described in Example 4, except that in this case CCompound18 was used as the starting material.

Example 6

The synthesis of CCompound23, N,N-diethyl-N-methyl-3-(2-methyl-3-9H-thioxanthen-9-ylidene)-propane-1-aminium-iodide The synthesis involved the following steps:
2-methylthioxanthon→9-[3-(diethylamino)propyl]-2-methyl-9H-thioxanthen-9-ol→N,N-diethyl-N-[3-(2-methyl-9H-thioxanthen-9-ylidene]-propyl amine→N,N,-diethyl-N-methyl-3-(2-methyl-9H-thioxanthen-9-ylidene)-propane-1-aminium-iodide.

Synthesis of 9-[3-(diethylamino)propyl]-2-methyl-9H-thioxanthen-9-ol (intermediate 1): 2-methylthioxanthone (4 g; 17.6 mmol) was dissolved in 50 ml of tetrahydrofuran. The thioxanthone solution was added drop-wise (over a 30 min period), during intensive mixing, to a solution (125 ml) containing 60 mmol of Grignard reagent (made as described under Example 2 using diethylaminopropyl chloride) and 100 ml of tetrahydrofuran. The mixture was refluxed for 5 hours followed by constant mixing at room temperature for 16 hours. Then the mixture was added to 500 ml of ice cold 50% saturated ammonium chloride followed by the collection of the organic phase. The water phase was extracted 3-times with 100 ml of ethylacetate. After drying the combined organic phase over water-free sodium sulfate, the solvent was removed by distillation. The resulting light yellow product (91% yield) was 99-100% pure as determined by NMR and thin layer chromatography (benzol:ethanol:water=50:15:3, by volume as solvent; Rf=0.41).

Synthesis of N,N-diethyl-N-[3-(2-methyl-9H-thioxanthen-9-ylidene]-propyl amine (intermediate 2): Intermediate 1 (4 g) was dissolved in a mixture of 94 ml water+5.37 ml concentrated $H_2SO_4$; then the mixture was refluxed for 1.5 hour with constant mixing. The mixture was added to 100 ml of ice-cold NaOH (pH 12) followed by extraction with 3×70 ml ethylacetate. Then 100 ml of 1 M HCl was added to the combined organic fraction to facilitate the transfer of the product from the organic phase to the acidic water phase. Next, solid $K_2CO_3$ was added to the acidic water phase to adjust the pH to about 12; this step was followed by extraction of the mixture with ethylacetate (3×70 ml). The combined organic phase was dried over water-free $Na_2SO_4$, followed by removal of the solvent by distillation. The resulting solid product was first dissolved in acetone/absolute ethanol, 1:1 by volume, mixture followed by the addition of concentrated HCl until the solid material (HCl salt) was formed. The solid precipitate was washed with cold acetone.

Synthesis of N,N-diethyl-N-methyl-3-(2-methyl-3-9H-thioxanthen-9-ylidene)-propane-1-aminium-iodide Two grams of intermediate 2 was dissolved in 10 ml water, followed by adjusting the pH to about 12 with 2 N NaOH; this mixture was then extracted with 2×20 ml of ethylacetate. The combined organic phase was dried over water-free $Na_2SO_4$, followed by removal of the solvent by distillation. The resulting material was dissolved in 10 ml of absolute acetone followed by the addition of 2 ml of methyl iodide. The mixture was first left for 12 hours at room temperature and then for 12 hours at 4° C. in a closed glass tube (to avoid contact with air). The solid product was filtered and washed with absolute acetone. The final product is a light yellow crystal which was 99-100% pure as verified by thin layer chromatography (TLC; benzol:ethanol:water=50:15:1.5, by volume as solvent) and NMR spectra.

Example 7

Synthesis of N,N,N-triethyl-3-(2-methyl-9H-thioxanthen-9-ylidene)-propane-1-aminium-iodide (CCompound25)

CCompound25 was synthesized by the same procedure described for CCompound23, except that in the last step 2 ml of ethyl iodide, instead of methyl iodide, was used.

Example 8

Synthesis of N,N-diethyl-N-allyl-3-(2-methyl-9H-thioxanthen-9-ylidene)-propane-1-aminium-bromide (CCompound26)

CCompound26 was synthesized by the same procedure described for CCompound23, except that in the last step 2 ml of allyl bromide, instead of methyl iodide, was used.

Example 9

Purification and Spectrophotometric Assay of PALP

Human PALP (Type XXIV, 1020 units of total activity) in a partially purified form was obtained commercially from Sigma-Aldrich. A butanol extraction of placental tissue, followed by ammonium sulfate precipitation and two chromatographic steps, was performed by Sigma-Aldrich to obtain the partially purified material. Butanol extraction inactivates most, if not all, of the other placental proteins, including growth factors, but does not reduce the mitogenic or enzymatic activity of PALP.

Figure 1:
FIG. 1 shows a picture of a gel separation, demonstrating that the PALP used for the animal experiments shown in Tables 6 to 10 was homogeneous or near homogeneous.

As determined by sodium dodecyl sulfate-polyacrylamide gel electrophoresis (SDS-PAGE), the partially purified PALP obtained from Sigma-Aldrich (denoted "commercial PALP" herein) was not homogeneous and contained other proteins. FIG. 1 shows a picture of a gel separation of a preparation comprising commercial PALP without further purification, and other preparations of PALP of increasing purity. Separation of proteins was performed by conventional SDS-PAGE, and proteins were stained with coomassie blue stain. Lane 1 contains various molecular mass standards for comparison. Lane 2 represents a preparation containing commercial PALP with a strong 52 kDa band representing $α_1$-antitrypsin and another strong 66 kDa band representing a mixture of PALP and albumin. Lanes 3 and 4 represent preparations comprising commercial PALP material after further purification steps (described below), and lane 5 represents a preparation of homogeneous PALP obtained by the complete purification procedure described below.

A purification procedure consisting of several steps was performed to further purify the commercially obtained PALP to homogeneity. A similar purification procedure described by Mukherjee et al. [She, Q.-B., Mukherjee, J. J., Huang, J.-S., Crilly, K. S. and Kiss, Z. (2000), "Growth factor-like effects of placental alkaline phosphatase in human and mouse embryo fibroblasts," FEBS Lett. 469, 163-167] was used, except that in embodiments of the invention the last chromatographic step was performed twice.

A solution of commercial PALP was prepared by dissolving 350 mg of commercial PALP into 10 ml of buffer A (0.1 M sodium acetate, 0.5 M NaCl, 1 mM $MgCl_2$, 1 mM $CaCl_2$, adjusted to pH 6.5). This solution was then further purified by successive Concanavalin A-Sepharose and Q-Sepharose chromatography, essentially following the procedure described elsewhere [Chang, T.-C., Huang, S.-M., Huang, T.-M. and Chang, G.-G. (1992), "Human placenta alkaline phosphatase: An improved purification procedure and kinetic studies," Eur. J. Biochem. 209, 241-247].

The solution was run through a Concanavalin A-Sepharose column followed by an elution step using buffer A as solvent. For elution, buffer A included 50 mM α-methyl-D-mannopyranoside. The active fractions collected from the effluent were pooled and dialyzed against buffer B (50 mM Tris-HCL at pH 7.7). SDS-PAGE separation of the collected and dialyzed fraction is shown in lane 3 of FIG. 1.

The collected and dialyzed fraction from the previous step was then passed through a Q-Sepharose column. The fraction of interest was eluted with buffer B using a linear gradient of 0-250 mM potassium phosphate at a pH of 7.5. The active fractions from the Q-Sepharose column were pooled and dialyzed against phosphate-buffered saline and concentrated by Amicon ultrafiltration. SDS-PAGE separation of the collected and dialyzed fraction is shown in FIG. 1 in lane 4, which demonstrates that at least two major proteins are still present in the fraction after dialysis.

Then, the collected and dialyzed fraction from the previous step was purified to homogeneity by t-butyl hydrophobic interaction chromatography (HIC). Prior to adding the fraction to the t-butyl HIC column, the fraction was made 2 M in ammonium sulfate, and pH was adjusted to 6.8. The 5 ml bed volume t-butyl HIC cartridge (BIO-RAD, Hercules, Calif.) was connected to a fast performance liquid chromatography (FPLC) system from PHARMACIA (Peapack, N.J.). The fraction was introduced to the HIC column, and the column was eluted with buffer C (100 mM sodium phosphate buffer, 2 M ammonium sulfate at pH 6.8). The column was eluted with buffer C until a first protein-containing fraction completely eluted, and then a negative gradient of 2 M-to-0 M ammonium sulfate in 100 mM sodium phosphate at pH 6.8 was passed over the column. The negative linear gradient was used to elute a second protein-containing fraction, which contained the enzymatically active PALP protein.

The enzymatically active fraction from the HIC separation was dialyzed against phosphate buffered saline and concentrated by Amicon ultrafiltration. Presence and purity of the PALP enzyme in the fraction was confirmed by SDS-PAGE. After electrophoretic separation, the gel was stained using coomassie blue or silver stain for visual observation of protein bands. In about 50% of cases a single protein band was observed with an approximate molecular weight of 66 kDa. In the other 50% of cases the PALP fraction still was slightly contaminated by α1-anti-trypsin, probably reflecting the higher amount of this protein in the starting commercial preparation. In these latter cases, the last chromatography step was repeated to entirely remove $\alpha_1$-anti-trypsin. The pure PALP was further identified by sequence analysis performed by the Mayo Clinic Protein Core Facility (Rochester, Minn., USA).

PALP enzyme activity was assayed using a spectroscopic method by monitoring the hydrolysis of 4-nitrophenylphosphate (as an increase in absorbance at 410 nm) at room temperature (22° C.) as described elsewhere [Chang, G.-G., Shiao, M.-S., Lee, K.-R. and Wu, J.-J. (1990), "Modification of human placental alkaline phosphatase by periodate-oxidized 1,$N^6$-ethenoadenosine monophosphate," Biochem. J. 272, 683-690]. Activity analysis of 5-10 μg purified enzyme was performed in 1 mL incubation volume containing 50 mM $Na_2CO_3$/$NaHCO_3$, 10 mM $MgCl_2$, 10 mM 4-nitrophenylphosphate at pH 9.8. The extinction coefficient of 4-nitrophenol was taken as $1.62 \times 10^4$ $M^{-1}$ $cm^{-1}$. An enzyme activity of 1 U (unit) is defined as 1 μmol substrate hydrolyzed/min at 22° C. at pH 9.8.

Example 10

Determination of Cell Viability

Cells that lost viability do not synthesize DNA. To quantify cell death, around the time when significant and characteristic morphological changes took place, cells were pulse-labeled for 10 minutes with [$^3$H]thymidine to measure DNA activity as described elsewhere [Tomono, M. and Kiss, Z. (1995), "Ethanol enhances the stimulatory effects of insulin and insulin-like growth factor-I on DNA synthesis in NIH 3T3 fibroblasts," Biochem. Biophys. Res. Commun. 208, 63-67]. Also, cells were collected as suspensions using trypsin, an established method in cell biology, followed by re-plating of cells in fresh tissue culture medium. If no viable cells were obtained after one week in culture, it meant that the cells at the time of re-plating were dead. Survival values obtained with untreated cells were considered 100%. For the determination of relative number of viable cells after treatments, in most cases the MTT assay was used. This calorimetric assay is based on the ability of living cells, but not dead cells, to reduce 3-(4,5-dimethyl thiazol-2-yl)-2,5-diphenyltetrazolium bromide [Carmichael, J, De Graff, W. G., Gazdar, A. F., Minna, J. D. and Mitchell, J. B. (1987), "Evaluation of tetrazolium-based semi-automated calorimetric assay: Assessment of chemosensitivity testing," Cancer Res. 47, 936-942]. For this assay, cells were plated in 96-well plates, and the MTT assay was performed both in untreated and treated cell cultures. The MTT assay also was performed at the start of treatments to allow assessment of proliferation rates in the control and treated cell cultures.

Example 11

Cell Lines and Cell Culture Reagents

Fetal bovine serum (FBS) and all tissue culture media were bought from Life Technologies (formerly GIBCO BRL) (Rockville, Md.). Except HaCaT keratinocytes (which were provided by the Institute of Dermatology, Szeged University, Szeged, Hungary) as well as MCF-7 and MCF-7/MDR1 cells (provided by the National Institute of Health, Bethesda, Md.), all other cell lines were provided by the American Type Culture Collection [Rockville, Md.].

Example 12

Determination of Effects of CCDTHT on Choline Metabolism in Cancer Cells

MEL-28 and MCF-7 cells were cultured in MEM medium supplemented with 10% fetal bovine serum (FBS) and in DMEM medium supplemented with 10% FBS, respectively. The AN3CA human endometrial adenocarcinoma cells were maintained in Eagle's MEM containing 10% FBS. Cancer cells were grown up to confluency in 12-well plates in 10% fetal-bovine serum-containing medium, then incubated in the presence of 1 μCi of [methyl-$^{14}$C]choline (bought from Amersham; Piscataway, N.J.) for 2 hours. Cells were first rapidly (within 30 seconds) washed three times with 4 ml of serum-free medium, then extracted with ice-cold methanol. This was followed by the determination of cellular free radiolabeled choline and phosphocholine (PCho) by column chromatography as described earlier [Kiss, Z. and Crilly, K. S. (1995), "Tamoxifen inhibits uptake and metabolism of ethanolamine and choline in multidrug-resistant, but not in drug-sensitive, MCF-7 human breast carcinoma cells," FEBS Lett. 360, 165-168], and the separation and determination of radiolabeled phosphatidylcholine (PtdCho) by thin layer chromatography as indicated in Kiss [Kiss, Z. (1996), "Direct proof that phorbol ester accelerates the use of choline phosphate for phosphatidylcholine synthesis in intact cells," Arch. Biochem. Biophys. 335, 191-196].

Example 13

Development and Treatment of Tumor Models

Tumors were developed in first generation hybrid BDF1 (C57 B1 female×DBA/2 male) adult female mice kept at specified pathogen free (SPF) hygienic level. Suspensions of HL-60 human leukemia cells, or approximately 0.1 cm$^3$ volume of tumor tissue derived from HT-168 human melanoma, PC-3 human prostate adenocarcinoma, T47D human breast carcinoma, MXT mouse mammary cancer, or mouse B16 melanoma cells were implanted subcutaneously to develop the tumors. After 12-18 days when the tumor-bearing mice were first treated, the size of the tumors was in the 0.2-0.4 cm$^3$ range. All compounds used were dissolved in physiological (0.9%) saline (NaCl), and the agents, alone or in combinations, were applied subcutaneously or intraperitoneally in 50 μl volume. Tumor volume was determined by calipers in three dimensions; this technique is well known to one having ordinary skill in the art. Tumor volume was calculated according to the generally accepted formula: $V=a^2 \times b \times \pi/6$, where "a" and "b" mean the shortest and longest diameter, respectively, of the measured tumor.

Examples showing that CCDTHT induces the death of cancer cells as indicated by their rounded-up morphology.

Example 14

CCDTHT Induces the Death of Human Melanoma MEL-28 Cells

Figure 2:
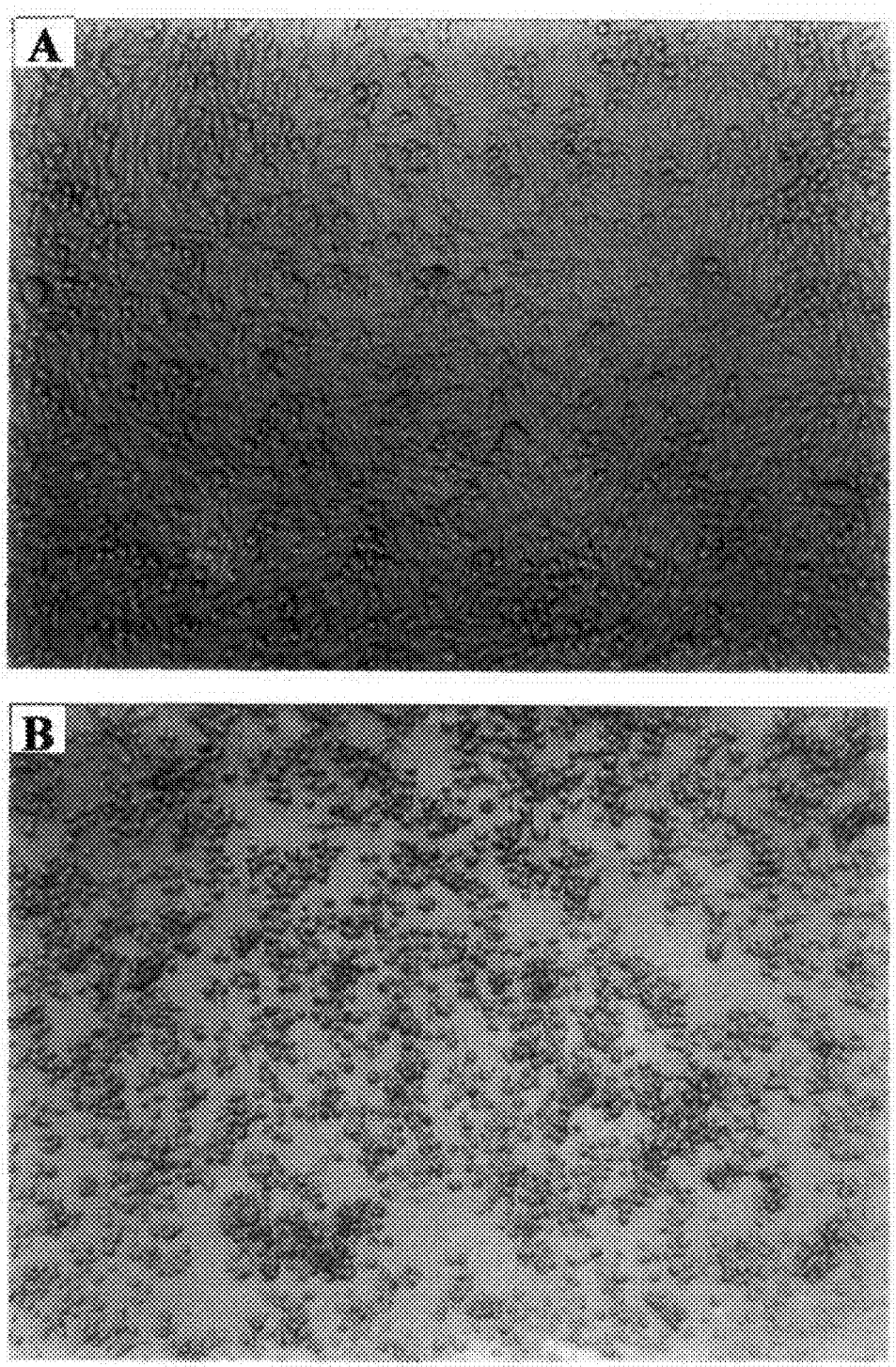
FIG. 2 is a digital image showing that unlike untreated human melanoma MEL-28 cells (A), MEL-28 cells treated with 100 μM CCDTHT (CCompound3) for 72 hours in 12-well plates were all rounded up, indicating death via one of the apoptotic pathways (B).

About 60% confluent cultures of MEL-28 cells, cultured in 12-well plates in MEM medium supplemented with 10% FBS, were either untreated (FIG. 2A), or were treated with 100 μM CCDTHT (CCompound3) for 72 hours (FIG. 2B). The pictures, taken 72 hours after the treatment, show that while the control cells reached the confluent state and remained healthy (FIG. 2A), the cell culture treated with CCDTHT (FIG. 2B) remained at about 60% confluent with practically all cells rounded up, indicating cell death via the apoptotic pathway. This experiment was repeated four times with similar results. In parallel experiments, cells treated for 72 hours with CCDTHT did not synthesize detectable amount of DNA as concluded from the absence of incorporation of radiolabeled thymidine into DNA. This indicates that the observed morphological changes were indeed associated with cell death.

Example 15

CCDTHT Induces the Death of Estrogen Positive Human Breast Cancer MCF-7 Cells

Figure 3:
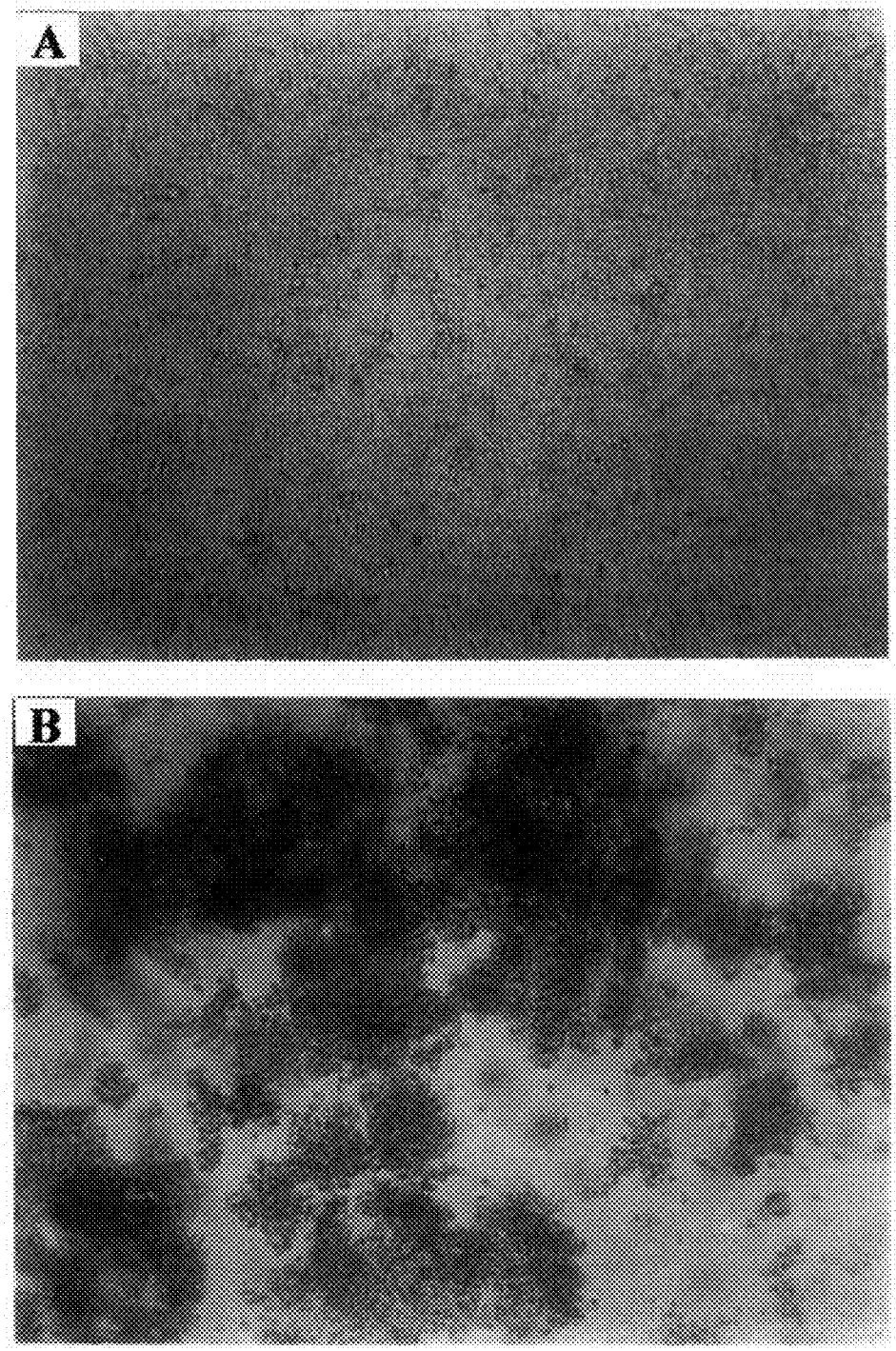
FIG. 3 is a digital image indicating that, compared to untreated human breast carcinoma MCF-7 cells (A), treatment of MCF-7 cells with 100 μM CCDTHT (CCompound3) for 72 hours (in 12-well plates) induced strong alterations in the morphology consistent with the death of all cells (B).

About 50% confluent cultures of MCF-7 cells, cultured in 12-well plates in Dulbecco's modified Eagle's medium (DMEM) supplemented with 10% FBS, were either untreated (FIG. 3A), or were treated with 100 μM CCDTHT (CCompound3) for 72 hours (FIG. 3B). The pictures, taken 72 hours after the treatment, show that the control cells reached a healthy confluent state (FIG. 3A). In contrast, the MCF-7 cell culture treated with CCDTHT (FIG. 3B) remained sub-confluent with practically all cells rounded up, again indicating cell death via the apoptotic pathway. This experiment was repeated three times with similar results. In some experiments, cells from the CCDTHT-treated cultures were seeded into 96-well plates, and the MTT assay was performed 96 hours later to test for viable cells. The MTT assay did not detect viable cells, indicating that (i) the above treatment with CCDTHT indeed killed practically all MCF-7 cells, and that (ii) the morphological pictures faithfully indicated cell death in CCDTHT-treated cell cultures.

Example 16

CCDTHT Induces the Death of Estrogen-Positive Human Breast Cancer T47D Cells

Figure 4:
FIG. 4 is an image illustrating that unlike untreated human breast carcinoma T47D cells (A), T47D cells treated with 100
Figure 4:
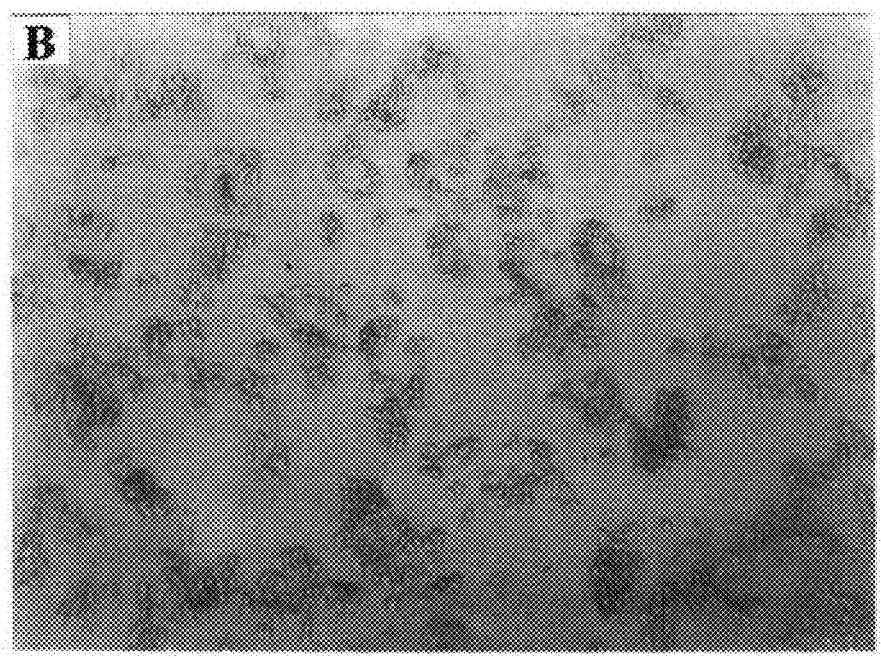
Figures 5A, 5B, 5C, 5D, 5E, 5F:
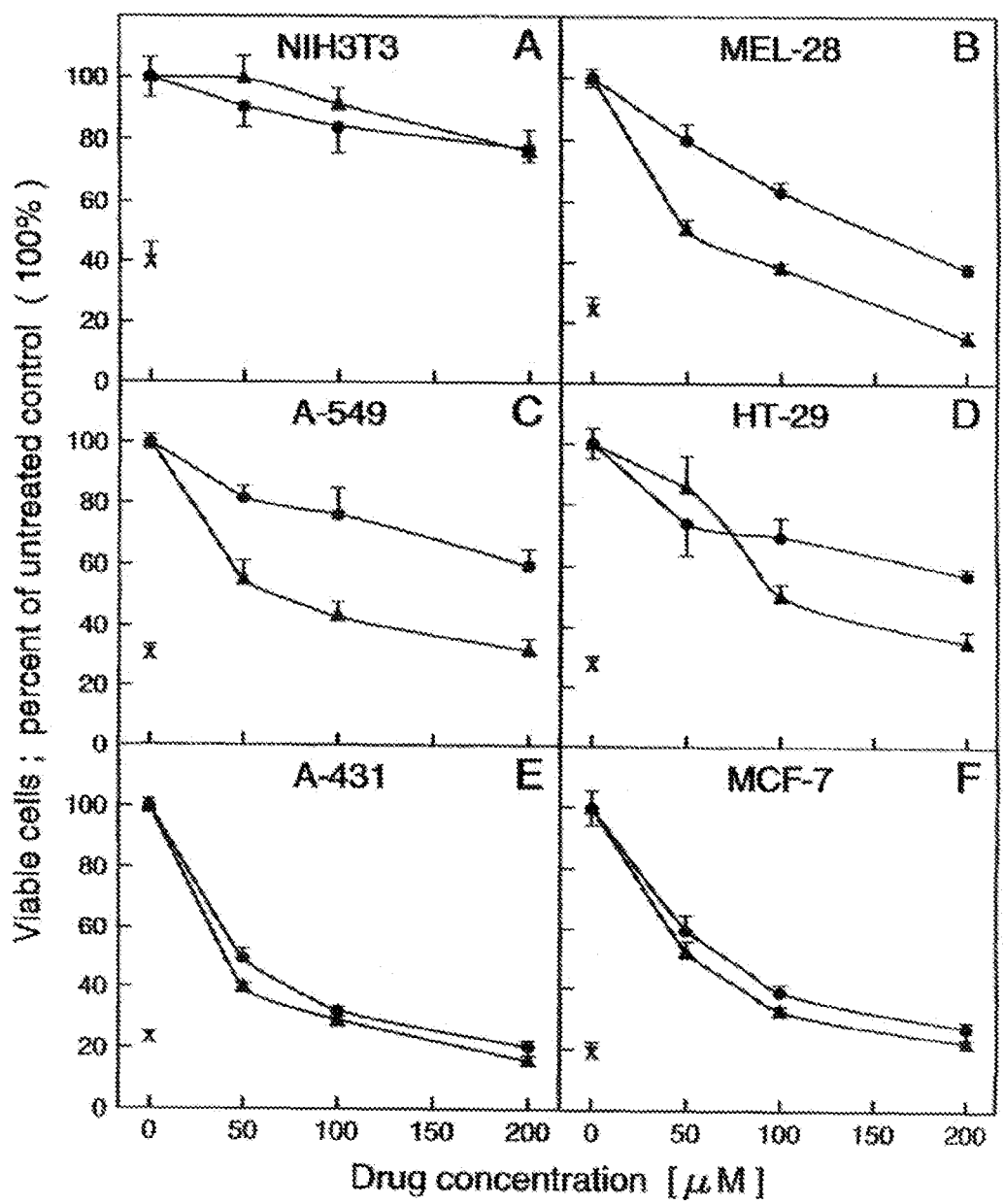

About 40% confluent cultures of T47D cells, cultured in 12-well plates in RPMI 1640 medium supplemented with 0.2 IU bovine insulin and 10% FBS, were either untreated (FIG. 4A), or were treated with 100 μM CCDTHT (CCompound3) for 72 hours (FIG. 4B). The pictures, taken 72 hours after the treatment, show that the control cells reached a healthy confluent state (FIG. 4A), while the T47D culture treated with CCDTHT (FIG. 4B) remained about 40% confluent with practically all cells rounded up, indicating cell death via the apoptotic pathway. This experiment was repeated three times with similar results. In some experiments, cells from the CCDTHT-treated cultures were seeded into 12-well plates to determine DNA synthesis 96 hours later; no DNA synthesis could be detected at that time point indicating that the above treatment with CCDTHT indeed killed practically all T47D cells.

Examples demonstrating the effects of CC compounds on the viability of normal and cancer cells using the MTT assay.

Example 17

Comparison of effects of CCompound1 and CCompound3 (CCDTHT) on the Viability of Normal and Cancer Cells The NIH 3T3 (normal) mouse fibroblast, A431 human epidermoid adenocarcinoma, and MCF-7 human breast cancer cells were cultured in DMEM medium containing 10% FBS. The MEL-28 human melanoma cells were cultured in MEM medium containing 10% FBS. The HT-29 human colon adenocarcinoma cells were cultured in McCoy's 5a medium containing 10% FBS. The A549 human lung carcinoma cells were maintained in Ham's F12K medium containing 10% FBS. Cells were seeded into 96-well plates and treated at ~70-90% confluency. Two hours before treatments the medium was changed for fresh 10% serum medium, and then the cells were incubated for 72 hours in the presence of 0-200 μM of CCompound1 (●) or CCompound3 (CCDTHT) (▲), as indicated. The MTT assay was used to determine cell viability after treatments. The values, shown in FIGS. 5A-5F and expressed as percent decrease in viability compared to the untreated control cells, are the mean±std. dev. of 8 incubations in one experiment. Similar results were obtained in another experiment. The data show that during the observation period none of these compounds exerted major toxic effects in the NIH 3T3 (normal) fibroblast cultures. In the MEL-28, A-549 and HT-29 cultures, CCDTHT was clearly more effective than CCompound1 in reducing cell numbers.

In the A-431 and MCF-7 cell lines, both agents exerted similarly large effects with CCDTHT being slightly more potent.

Example 18

Long-Term Effects of CCDTHT on the Viability of Normal and Cancer Cells

NIH3T3, T47D, A-431, HT-29, and MEL-28 cells were cultured as indicated earlier. CaOV-3 human ovarian cancer cells were cultured in DMEM containing 10% FBS. ZR-75-1 human estrogen receptor-positive breast cancer cells were maintained in RPMI 1640 medium supplemented with 10% FBS. HTB-157 human fetal fibroblasts, MEL-24 human malignant melanoma cells, Hep G2 human hepatoblastoma cells, and CaCO-2 human colon adenocarcinoma cells were maintained in Eagles's MEM containing 10% FBS. MB-231 human estrogen receptor-negative breast cancer cells were maintained in Leibovitz's L-15 medium supplemented with 10% FBS. Cells were seeded into 96-well plates and treated at ~70-90% confluency. Two hours prior to treatments the medium was changed for fresh 10% serum medium, and then the cells were incubated for 10 days in the absence (□) or presence of 50 μM CCDTHT (☒)or 100 μM CCDTHT (■). The medium was changed and the cells were re-treated on days 3 and 6. The MTT assay was used to determine cell viability on day 10. The data, shown in FIG. 6, are the mean±std. dev. of 8 incubations in one experiment. (The experiment was repeated twice with similar results). The results show that 100 μM CCDTHT causes 50% or less reduction in the number of viable cells in case of the two normal cell lines (HTB-157 and NIH 3T3 cells) and three cancer cell lines (MEL-24, HT-29, and CaCO-2). The T47D, ZR-75-1, CaOV-3, A-431 and MEL-28 cells were very sensitive, while the MB-231 and HepG2 cells were moderately sensitive to the inhibitory actions of CCDTHT. Clearly, 100 μM CCDTHT does not universally induce strong reduction in the viability of all types of cancer cells.

Example 19

Effects of CCDTHT on the Viability of Malignant Glioma Cells and Astrocytomas The U-87 human malignant glioma cells were cultured in MEM supplemented with 10% FBS. The CCF-STTG1 human grade IV astrocytoma cells were maintained in RPMI 1640 containing 1 mM glutamine and 10% FBS. Cells were seeded into 12-well plates and treated at 60-70% confluency. Two hours prior to the treatments the medium was changed for fresh 10% serum medium, and then cells were incubated for 72 hours in the absence (□) or presence of 50 μM CCDTHT (◨), 100 μM CCDTHT (◫), 150 μM CCDTHT (☒), or 200 μM CCDTHT (■). The MTT assay was used to determine cell viability. The data, shown in FIG. 7, are the mean±std. dev. of 8 incubations in one experiment (the experiment was repeated once with similar results). The results demonstrate that 100-200 μM concentrations of CCDTHT sharply decrease the number of viable U-87 and CCF-STTG1 cells. This suggests that CCDTHT may be particularly effective against the most dangerous forms of brain cancer.

Example 20

Comparison of CCompounds on the Viability of Normal MRC-5 Lung Fibroblasts as Well as T47D Breast Cancer and CaOV-3 Ovary Cancer Cells The MRC-5 cell line is derived from normal lung tissue of a 14-week-old male fetus. MRC-5 cells were maintained and treated in Eagles Medium with Hanks' BSS containing 10% fetal bovine serum. The T47D cells were maintained and treated in RPMI 1640 medium supplemented with 0.2 IU bovine insulin and 10% fetal bovine serum. The CaOV-3 human ovarian cancer cells were cultured in Dulbecco's modified Eagle's medium containing 10% fetal bovine serum. The cells were seeded in 96-well plates either at 10,000 cells per well or 30,000 cells per well to examine the antiproliferative and cytotoxic effects of various CC compounds, respectively. The cells were incubated for 24 hours, then the medium was changed followed by the treatments of cultures 2 hours after the medium change. At this point, cell cultures seeded at 10,000 cells per well and 30,000 cells per well were 25-35% and 80-90% confluent, respectively. Incubations were continued for 72 hours followed by the MTT assay. The data, shown in TABLE 2, indicate the inhibitory concentrations of CC compounds ($IC_{50}$) required for 50% decrease in the number of viable cells. These numbers are calculated from the mean of 4 incubations in one experiment (the experiment was repeated once with similar results). The results indicate that while the ovary cancer cells are the most sensitive to CCompound24, in case of the T47D cancer cells CCompound26 had the greatest inhibitory effects. It is also clear that while in case of CaOV-3 cells CCDTHT (CCompound3) was more effective than CCompound26, in case of T47D cells CCompound26 was superior to CCDTHT. What is also important is that significantly greater concentrations of these CC compounds were required to inhibit the proliferation of normal fibroblasts (MRC-5 cells) than that of these cancer cells. This suggests that at least in case of cancers of the breast and ovary, CC compounds may be used to control tumor growth without significantly impacting the normal tissues.

TABLE 2

Comparison of CC compounds on the viability of normal MRC-5 lung fibroblasts as well as T47D breast cancer and CaOV-3 ovary cancer cells.

| | $IC_{50}$ values | | | | | |
|---|---|---|---|---|---|---|
| | Antiproliferative | | | Cytotoxic | | |
| CC compound | MRC-5 | T47D | CaOV-3 | MRC-5 | T47D | CaOV-3 |
| CCcompound3 | 90 | 47 | 38 | 119 | 66 | 39 |
| CCcompound21 | 113 | 76 | 32 | 164 | 59 | 29 |
| CCcompound22 | 140 | 65 | 61 | 215 | 65 | 36 |
| CCcompound23 | 139 | 48 | 14 | 163 | 38 | 32 |
| CCcompound24 | 113 | 56 | 69 | 207 | 59 | 29 |
| CCcompound25 | 118 | 18 | 47 | 123 | 39 | 66 |
| CCcompound26 | 86 | 11 | 57 | 98 | 8 | 59 |

Example 21

The Reversibility of CCDTHT Action on Cell Viability

HTB-157, MEL-28, CaOV-3, T47D, and A-431 cells were maintained as indicated earlier. The 3A-SubE post crisis placenta cells (capable of unlimited proliferation) were maintained in Eagle's MEM containing 10% FBS. Cells were seeded into 96-well plates and treated at ~70-90% confluency. Two hours before treatments the medium was changed for fresh 10% serum medium, and then cells were incubated for 48 hours in the absence (□) or presence of 50 μM CCDTHT (⊠)or 100 μM CCDTHT (■). Half of the cultures was analyzed by the MTT assay at this point, and the other half of the cultures was incubated for an additional 96 hours in fresh 10% serum-containing medium without CCDTHT followed by the MTT assay. The data, shown in FIG. 8, are the mean±std. dev. of 8 incubations in one experiment. (Similar results were obtained in another experiment). HTB-157 (normal) cells, but none of the cancer cell types, clearly resumed proliferation in fresh medium following the treatment with 100 μM CCDTHT. In some cases (MEL-28 and 3A-SubE cells), pre-treatment with 50 μM CCDTHT was not sufficient to suppress proliferation. Overall, these results again indicate that a relatively high dose of CCDTHT can irreversibly block proliferation of cancer cells, while normal cells can resume proliferation more effectively.

too toxic to normal cells, precluding its use in vivo. Also, for the treatment of ovarian cancer and breast cancer, CCDTHT seems to be the best choice (although in this experiment CCompounds21-26 were not tested). In contrast, CCompound12 or combination of CCompound12 with CCompound11 or CCompound14 appears to be the most effective against melanoma. Similar comparative studies were also performed with A-431 human epidermoid adenocarcinoma cells (CCDTHT, CCompound9, and CCompound12; 68-74% inhibition), PC-3 human prostate cancer cells (CCDTHT and CCompound11; 54-55% inhibition), A549 human lung adenocarcinoma cells (CCompound11; 68% inhibition), MB-231 human estrogen receptor-independent breast cancer cells (CCompound11; 75% inhibition), and HT-29 human colon adenocarcinoma cells (CCompound11 and CCompound14; 63-71% inhibition). The CC compounds indicated in the parentheses are the most effective inhibitors of proliferation of the respective cancer cell lines.

TABLE 3

Comparison of the effects of selected CC compounds (100 μM) on the number of normal and cancer cells.

| CC compound | Decrease in cell number (maximal decrease = 100%) | | | | | | |
|---|---|---|---|---|---|---|---|
| | NIH 3T3 | OVCAR | CaOV-3 | MEL-24 | MEL-28 | ZR-75-1 | T47D |
| CCDTHT | 29 | 63 | 84 | 15 | 60 | 74 | 61 |
| CCcompound8 | 93 | 25 | 93 | 79 | 90 | 43 | 60 |
| CCcompound9 | 22 | 41 | 45 | 4 | 14 | 70 | 52 |
| CCcompound10 | 21 | 38 | 45 | 15 | 11 | 65 | 51 |
| CCcompound11 | 21 | 62 | 66 | 20 | 94 | 75 | 59 |
| CCcompound12 | 0 | 30 | 80 | 73 | 71 | 17 | 48 |
| CCcompound13 | 25 | 27 | 53 | 12 | 11 | 48 | 47 |
| CCcompound14 | 30 | 65 | 69 | 21 | 90 | 53 | 58 |
| CCcompound15 | 11 | 26 | 28 | 0 | 19 | 41 | 35 |
| CCcompound16 | 19 | 0 | 12 | 0 | 10 | 39 | 48 |

Example 22

Comparison of the Effects of Structurally Similar CC Compounds on the Proliferation of Normal and Cancer Cells This experiment was performed to examine (i) how the melanoma cell line pairs (MEL-24 and MEL-28 cells), ovarian cancer cell line pairs (OVCAR and CaOV-3 cells), and estrogen positive breast cancer cell line pairs (T47D and ZR-75-1), in each case two cell lines being derived from similar tumors, respond to different CC compounds, and (ii) if any of the CC compounds are too toxic to normal cells (such as NIH 3T3 cells) which would preclude their use as anticancer agents. NIH 3T3, MEL-28, MEL-24, CaOV-3, ZR-75-1, and T47D cells were cultured as described above. The OVCAR human ovarian cancer cells were cultured in DMEM containing 10% FBS. Cells were seeded into 96-well plates and used at ~60-80% confluency. Two hours before treatments the medium was changed for fresh 10% serum medium, and then the cells were incubated for 72 hours in the absence or presence of 100 μM of each of CC compounds as listed in TABLE 3. The inhibitory effects of CC compounds on cell proliferation are expressed as percent decrease compared to untreated cell cultures (the greater the number, the greater the inhibitory effect of the CC compound). The data (average of 8 determinations) indicate that CCompound8 is Examples comparing the effects of CCDTHT and the choline transport/choline kinase inhibitor hemicholinium-3 (HC-3) on choline metabolism and cell proliferation.

Example 23

Comparison of Inhibitory Effects of Hemicholinium-3 (HC-3) and CCDTHT on Choline Metabolism in Cancer Cells MCF-7 and MEL-28 cells were cultured as described earlier. The AN3CA human endometrial adenocarcinoma cells were maintained in Eagle's MEM containing 10% FBS. Each cell type was grown in 12-well plates to confluency and then incubated with 1 μCi of [methyl-$^{14}$C]choline for 2 hours in the absence (□) or presence of 100 μM CCDTHT (⊠)or 0.5 mM HC-3 (■), followed by the determination of cellular contents of radiolabeled choline (A), PCho (B) and PtdCho (C), as indicated in FIG. 9. In each cell line, CCDTHT and HC-3 exerted comparably strong inhibitory effects on choline uptake and metabolism. Thus, if both CCDTHT and HC-3 influenced cell viability solely via inhibition of choline metabolism, then these agents should similarly affect cell viability, at least at the concentrations used in the choline transport experiment. It should be noted here, that at 0.1 mM concentration HC-3 was a relatively weak inhibitor of choline transport (20-25% inhibition; data not shown here).

Example 24

Comparison of Effects of CCDTHT and HC-3 on the Viability of Cancer Cells

AN3CA, HT-29, MEL-28, and MCF-7 cells were cultured as described earlier. Cells were seeded into 96-well plates; when cells were ~60-90% confluent, the medium was changed for fresh 10% serum-containing medium, followed by incubations for 72 hours in the absence (□) or presence of 100 μM CCDTHT (⊠)or 0.5 mM HC-3 (■). The MTT assay was used to determine cell viability. The data, shown in FIG. 10, are the mean±std. dev. of 8 incubations in one experiment. The results show that in AN3CA, HT-29, and MEL-28 cells, but not in MCF-7 cells, 100 μM CCDTHT causes much greater decreases in the number of viable cells compared to 0.5 mM HC-3. The data are consistent with the idea that in MCF-7 cells CCDTHT decreases cell viability purely via inhibiting choline metabolism, while in the other cell types CCDTHT acts by an additional mechanism probably either involving changes in the mitochondrial membrane and/or a presently unknown mechanism.

Example 25

Ethanolamine Prevents the Effects of CCDTHT on Cell Viability only in MCF-7 Cells NIH 3T3, AN3CA, HT-29, MEL-28, and MCF-7 cells were cultured as described earlier. Cells were seeded into 96-well plates; when cells were ~80-90% confluent, the medium was changed for fresh 10% serum-containing medium, followed by incubations for 72 hours in the absence (□) or presence of 100 μM CCDTHT (⊠), 2 mM ethanolamine (Etn) (⊠), or 100 μM CCDTHT+2 mM Etn (■). The MTT assay was used to determine cell viability. The data, shown in FIG. 11, are the mean±std. dev. of 8 incubations in one experiment. In MCF-7 cells, but not in the other cancer cell lines, Etn clearly prevented the CCDTHT-induced reduction in cell viability. While the reason for this is not entirely clear, this suggests that CCDTHT inhibits cell proliferation by Etn-inhibited and non-inhibited mechanisms, and that in MCF-7 cells CCDTHT acted mostly via the former mechanism(s).

Examples demonstrating the efficacy of CCDTHT in inhibiting proliferation of HaCaT keratinocytes.

Example 26

CCDTHT Induces the Death of HaCaT Keratinocytes but not Human Fetal Fibroblasts Treatment for 48 Hours HaCaT keratinocytes, frequently used immortalized model cells for studying psoriatic keratinocytes, and HTB-157 human fetus lung fibroblasts were cultured in 10% FBS-containing Dulbecco's modified Eagle's medium (DMEM). Cells were distributed in 96-well plates; when cells were 50-60% confluent, the medium was changed for fresh 10% serum-containing medium, followed by incubations for 48 hours in the absence (□) or presence of 50 μM CCDTHT (⊠), or 100 μM CCDTHT (■). The MTT assay was used to determine cell viability. The data, shown in FIG. 12, are the mean±std. dev. of 8 incubations in one experiment (the experiment was repeated once with similar results). While in HaCaT cells, 50-100 μM CCDTHT strongly (by 85-98%) reduced the number of viable cells, in HTB-157 fibroblasts this compound had much smaller effects (20-22% decrease in viability). Parallel microscopic examination of treated cells revealed that CCDTHT strongly altered the morphology of HaCaT cells, consistent with cell death, while CCDTHT had no visible effect on the morphology of HTB-157 cells. Also, in HaCaT cells, 100 μM CCDTHT inhibited DNA synthesis by about 95% after treatment for 48 hours, while a similar treatment caused only about 16% decrease in DNA synthesis in the fibroblasts. Furthermore, when after treatment with CCDTHT the HaCaT cells were re-plated, no viable cells were found after incubations in fresh medium for 1 week. In contrast, there was practically no difference between the numbers of re-plated untreated and treated (100 μM CCDTHT) HTB-157 fibroblasts. This was a clear indication that the effects of CCDTHT on the viability of HaCaT cells, unlike its smaller effects on the viability of normal fibroblasts, were irreversible.

Example 27

Demonstration that after Treatment for 72 Hours CCDTHT Preferably Decreases the Viability of HaCaT Cells Compared to Fibroblasts HaCaT cells as well as HTB-157 and mouse embryo NIH 3T3 fibroblasts were similarly maintained in 10% FBS-containing DMEM, while 966 SK human skin fibroblasts were maintained in 10% serum-containing MEM. Cells were distributed in 96-well plates; when cells were ~60-80% confluent, the medium was changed for fresh 10% serum-containing medium, followed by incubations for 72 hours in the absence (□) or presence of 50 μM CCDTHT (⊠), or 100 μM CCDTHT (■). The MTT assay was used to determine cell viability. The data, shown in FIG. 13, are the mean±std. dev. of 8 incubations in one experiment (the experiment was repeated once with similar results). Clearly, the data show that even after longer treatments, the three different fibroblast lines are significantly less sensitive toward the inhibitory actions of CCDTHT than the HaCaT cells.

Comparison of effects of CCDTHT on four different cancer cell types in vitro and after transplantation in vivo.

In these experiments the effects of CCDTHT were examined on the viability and growth of the same four tumor cell types in vitro as well as in vivo after transplantation.

Example 28

Comparison of the Effects of CCDTHT on the Viability of Various Types of Human Cancer Cells In Vitro PC-3 human prostate adenocarcinoma cells were cultured in 12-well plates in Ham's F12 cell culture medium supplemented with 7% fetal bovine serum; the medium was changed for fresh 10% medium 2 hours prior to treatments. HL-60 human leukemia cells (in flasks) and HT 168 human melanoma cells were cultured in RPMI 1640 medium supplemented with 10% FCS; treatment of HL-60 and HT-168 cells were performed in flasks and 12-well plates, respectively. T47D cells were cultured in 12-well plates in RPMI 1640 medium supplemented with 2 mM L-glutamine, 10 mM Hepes, 1 mM sodium pyruvate, 4.5 g/L glucose, 1.5 g/L sodium bicarbonate, 0.2 I.U. bovine insulin/ml, and 10% fetal bovine serum; the medium was changed for fresh 10% serum-containing medium 2 hours prior to treatments. All cells were incubated for 96 hours in the absence (□) or presence of 25 μM CCDTHT (▨), 50 μM CCDTHT (▧), or 75 μM CCDTHT (■). In this experiment, the viability of the cell cultures was estimated by Trypan blue exclusion using hematocytometer, a technique well known to one having ordinary skill in the art. Three independently treated cell cultures, involving at least 300 cells for each treatment, were analyzed. The experimental error is indicated as std. dev. The results, shown in FIG. 14, indicate that the treatments with 50-75 μM concentrations of CCDTHT for four days strongly decreased the number of viable cancer cells; the HT-168, PC-3 and T47D cells were the most sensitive to the actions of CCDTHT. The experiment with T47D cells particularly well demonstrates that, in comparison to previous experiments with the same cell lines, the effect of CCDTHT in vitro is delayed but can be very powerful if sufficient time is allowed for its action to develop (i.e., 96 hours instead of 72 hours).

Example 29

Effects of CCDTHT Alone on the Growth of Experimental Human Tumors

The experimental HL-60, HT-168, PC-3 and T47D human tumors were developed in mice as described above. FIG. 15 depicts the effects of 50 μmole (▨), 100 μmole (▧), 200 μmole (▩), and 400 μmole CCDTHT (■), injected subcutaneously once daily, on the growth of these human tumor xenografts. "□" indicates the corresponding values in the untreated tumors. In a, b, c, and d, treatments started on day 18, 17, 12 and 17, respectively, and they were performed for 5+3 days, 5+5 days, 5+3 days and 5+5 days, respectively, in each case with 2 treatment-free days inserted between the 2 series of treatments. Treatments were terminated on day 29, 30, 23, and 30, respectively. Data, representing the average tumor size of 5 tumor-bearing mice for each treatment, is expressed as % of the control tumor volume (untreated; 100%). The results indicate that 200-400 μmole amounts of CCDTHT considerably reduced the growth of each tumor with the largest response being elicited in case of the HL-60 leukemia tumors. In none of the cases did CCDTHT cause significant weight loss, and the animals survived, on average, 3 to 8 days longer than without treatment.

Examples showing that CCDTHT is more effective in the presence of pyrrolidinedithiocarbamate, zinc, and ethacrynic acid in reducing tumor volume.

Example 30

Effects of CCDTHT Alone and in Combination with Pyrrolidinedithiocarbamate (PC)+Zinc (Zn) on the Growth of HT-168 Human Melanoma Experimental Tumors The HT-168 human melanoma tumors were developed as described above. They were untreated (●), or treated once daily between 17-30 days on days 17, 18, 19, 20, 21, 24, 25, 26, 27, and 28 with 200 μmole CCDTHT (▲), 100 μmole PC+100 μmole Zn (■), or 200 μmole CCDTHT+100 μmole PC+100 μmole Zn (♦). Each group consisted of 5 animals, and the mean values are presented (the differences between the lowest and highest values were always less than 11%). As shown in FIG. 16, the inhibitory effect of CCDTHT on melanoma tumor growth was enhanced by PC+Zn in an additive manner or even synergistically (at later time points). The mechanism of combined effect of PC and Zn is the subject of the U.S. Pat. No. 6,756,063, titled "Methods and compositions for the treatment of human and animal cancers"; issued on Jun. 29, 2004. In short, PC acts as a carrier for Zn through the cell membrane; i.e., PC is able to carry Zn inside the cells which, if zinc achieves a certain intracellular concentration, can lead to cell death. Considering that CCDTHT had effects on tumor size in several randomly selected tumors, it is a reasonable expectation that CCDTHT in combination with PC and Zn will effectively inhibit the growth of many different tumors. Based on the differential effects of various CC compounds on the viability and proliferation of different types of cancer cells, it is also reasonable to expect that different tumors will exhibit different sensitivity toward CC compounds, so that CCDTHT may in some tumors be less effective than other CC compounds.

Examples showing that CCDTHT enhances the effects of Cisplatin (CisPt) on tumor volume while decreasing its toxic effects.

Example 31

Combined Effects CCDTHT and CisPt on the Growth of MXT Tumor as Well as Body Weight and Survival of the Experimental Animals The mouse mammary MXT tumor was developed as described above. On day 7 after transplantation of tumor cells, the animals were either remained untreated (group 1) or were treated with 2 mg/kg of CisPt alone (Group 2), or 4 mg/kg of CisPt alone (Group 3), or 4.6 mg/kg of CCDTHT alone (Group 4), or 2 mg/kg of CisPt+4.6 mg/kg of CCDTHT (Group 5), or 4 mg/kg of CisPt+4.6 mg/kg of CCDTHT (Group 6). CCDTHT and CisPt were administered subcutaneously and intraperitoneally, respectively, once daily for 10 days, including a 2-day rest period after 5 days of treatment (i.e., the last treatment was on day 19). Each group consisted of 7 animals, and the mean values±std. dev. for tumor volumes and body weight are shown in TABLE 4 and TABLE 5, respectively. While in this tumor model CCDTHT alone reduced the tumor volume less effectively than in the human tumor models, it clearly added to the tumor volume-reducing effect of CisPt (TABLE 4). A dramatic reduction in tumor volume was particularly evident in Group 6 (4 mg/kg CisPt+ 4.6 mg/kg CCDTHT). This experiment indicated that CCDTHT may be used to enhance the effects of chemotherapeutic agents on tumor volume.

As shown in TABLE 5, treatments with CisPt, particularly with the larger dose, caused significant decrease in body weight as a clear sign of toxic effects on normal tissues. While CCDTHT alone had no effect on body weight, it partially prevented CisPt-induced decrease in body weight at both concentrations of the latter.

TABLE 4

CCDTHT and CisPt in combination have greater effects on tumor volume than separately in the MXT tumor model.

| Group | Treatment | Tumor volume (cm$^3$) | | | |
|---|---|---|---|---|---|
| | | Day 7 | Day 14 | Day 18 | Day 21 |
| 1 | None | 0.44 ± 0.07 | 5.24 ± 0.27 | 8.61 ± 0.62 | 11.54 ± 1.36 |
| 2 | CisPt, 2 mg/kg | 0.46 ± 0.08 | 3.34 ± 1.04 | 5.37 ± 0.68 | 6.23 ± 0.86 |
| 3 | CisPt, 4 mg/kg | 0.45 ± 0.10 | 1.77 ± 0.40 | all dead | all dead |
| 4 | CCDTHT, 4.6 mg/kg | 0.43 ± 0.07 | 4.14 ± 0.71 | 6.62 ± 0.43 | 9.35 ± 0.69 |
| 5 | CisPt, 2 mg/kg + CCDTHT, 4.6 mg/kg | 0.48 ± 0.12 | 2.88 ± 0.47 | 4.69 ± 0.79 | 5.32 ± 0.46 |
| 6 | CisPt, 4 mg.kg + CCDTHT, 4.6 mg/kg | 0.43 ± 0.15 | 1.64 ± 0.37 | 2.51 ± 0.35 | 3.76 ± 0.31 |

TABLE 5

CCDTHT partially prevents CisPt-induced reduction in body weight in the MXT tumor model.

| Group | Treatment | Body weight (g) | | | |
|---|---|---|---|---|---|
| | | Day 7 | Day 14 | Day 18 | Day 21 |
| 1 | None | 22.9 ± 0.89 | 25.6 ± 1.07 | 27.3 ± 0.70 | 29.6 ± 1.52 |
| 2 | CisPt, 2 mg/kg | 22.4 ± 0.73 | 22.9 ± 0.87 | 22.3 ± 1.02 | 21.2 ± 1.31 |
| 3 | CisPt, 4 mg/kg | 22.5 ± 0.92 | 19.4 ± 1.05 | all dead | all dead |
| 4 | CCDTHT, 4.6 mg/kg | 22.8 ± 0.82 | 25.1 ± 0.84 | 26.9 ± 0.93 | 28.8 ± 0.91 |
| 5 | CisPt, 2 mg/kg + CCDTHT, 4.6 mg/kg | 22.5 ± 0.95 | 22.6 ± 0.53 | 24.2 ± 0.90 | 27.0 ± 1.51 |
| 6 | CisPt, 4 mg.kg + CCDTHT, 4.6 mg/kg | 22.3 ± 1.06 | 22.3 ± 1.50 | 23.6 ± 1.59 | 25.9 ± 1.30 |

On average, control animals survived for 26.8±2.4 days, while animals in groups 2, 3, 4, 5, and 6 survived for 32.7±6.2, 18.1±0.7, 30.6±3.2, 34.7±5.4 and 25.1±3.3 days, respectively. The most dramatic effect of CCDTHT was its ability to enhance the survival of 4 mg/kg CisPt-treated group from 18 to 25 days. It clearly indicates that the simultaneous use of CCDTHT allows the use of higher, more effective doses of CisPt, and by implication of other chemotherapeutic agents. It should be noted that most animals with large treated tumors died because of various lung problems. Since in humans there are effective methods to protect the lung's functions, it is reasonable to expect that the effect of CCDTHT on the survival of CisPt-treated human patients will prove to be even greater.

Examples showing that placental alkaline phosphatase (PALP) alone or in combination with CisPt exhibits anticancer effects.

Example 32

Combined Effects of PALP and CisPt on the Growth of MXT Tumor as Well as Body Weight and Survival of the Experimental Animals The mouse mammary MXT tumor model was developed and treated as described above. On day 7 the animals were either remained untreated (Group 1) or were treated with 3 mg/kg of CisPt (Group 2) or 3 mg/kg of CisPt+15 mg/kg of highly purified PALP (Group 3). CisPt and PALP were administered intraperitoneally and subcutaneously, respectively, seven times on every second day (i.e., treatments were terminated on day 21). Each group included 7 animals; the mean values±std. dev. for tumor volumes and body weight are shown in TABLE 6 and TABLE 7, respectively. The data show that on each day examined, PALP consistently enhanced the inhibitory effects of CisPt on tumor growth (TABLE 6). In addition, PALP fully restored body weight lost as a consequence of CisPt treatment (TABLE 7).

Probably as a combination of effects of PALP on tumor volume, PALP also enhanced the survival of animals. While the control and CisPt-treated animals survived for 24.2±2.2 and 31.1±6.2 days, respectively, the CisPt+PALP-treated animals survived for 37.7±3.68 days. Based on these results, it is reasonable to expect that PALP will enhance the efficacy of other cancer treatments as well with parallel extension of survival time and reduction of body weight loss.

TABLE 6

PALP enhances the inhibitory effects of CisPt on the growth of MXT tumors.

| Group | Treatment | Tumor volume (cm$^3$) | | | |
|---|---|---|---|---|---|
| | | Day 7 | Day 11 | Day 16 | Day 21 |
| 1 | None | 0.35 ± 0.09 | 2.94 ± 0.75 | 7.98 ± 1.25 | 11.13 ± 2.70 |
| 2 | CisPt | 0.38 ± 0.01 | 1.45 ± 0.22 | 4.53 ± 1.00 | 5.86 ± 1.38 |
| 3 | CisPt + PALP | 0.33 ± 0.06 | 1.16 ± 0.24 | 3.32 ± 0.87 | 4.28 ± 0.97 |

TABLE 7

PALP prevents CisPt-induced body weight loss in the MXT tumor model.

| Group | Treatment | Body weight (g) | | | |
|---|---|---|---|---|---|
| | | Day 7 | Day 11 | Day 16 | Day 21 |
| 1 | None | 22.3 ± 0.61 | 24.5 ± 0.91 | 25.9 ± 1.13 | 27.7 ± 1.34 |
| 2 | CisPt | 22.7 ± 0.37 | 23.1 ± 0.52 | 20.9 ± 0.65 | 19.2 ± 0.66 |
| 3 | CisPt + PALP | 22.1 ± 0.52 | 24.2 ± 0.27 | 25.6 ± 0.26 | 27.1 ± 0.49 |

Examples showing that CCDTHT in combination with PALP has greater anticancer effects than alone.

Example 33

CCDTHT in Combination with PALP More Effectively Inhibits the Growth of Leukemia Tumor and Promotes Survival than Alone The HL-60 human leukemia model was developed and treated as described above. On day 12 the mice either remained untreated (Group 1) or were treated with 4.6 mg/kg CCDTHT (Group 2) or 4.6 mg/kg CCDTHT+15 mg/kg highly purified PALP (Group 3). Both CCDTHT and PALP were administered subcutaneously for three 5-day cycles with 2 resting days included between each 5-day cycle. In each group 7 mice were included. The mean values std. dev. for tumor volumes are shown in TABLE 8. The data show that CCDTHT inhibits the growth of leukemia tumor and that CCDTHT+PALP have greater inhibitory effects than CCDTHT alone.

The two agents had even more pronounced combined effects on the survival of leukemic mice. While the untreated mice survived for 28.9±3.4 days, mice treated with CCDTHT alone and CCDTHT+PALP survived for 34.9±6.6 and 46.3±9.7 days, respectively. The remarkable 60% increase in survival by CCDTHT+PALP is a strong indication that human leukemia may be one of those cancers where the CCDTHT/PALP combination, probably in combination with other therapies, can be used successfully to control cancer cell growth and enhance survival.

Example 34

CCDTHT and PALP in Combination Restore Body Weight and Enhance the Inhibitory Effects of CisPt on the Growth of MXT Tumors The mouse mammary MXT tumor model was developed and treated as described above. On day 7 the animals either remained untreated (Group 1) or were treated with 3 mg/kg CisPt (Group 2), 3 mg/kg CisPt+4.6 mg/kg of CCDTHT (Group 3), or 3 mg/kg CisPt+4.6 mg/kg of CCDTHT+15 mg/kg highly purified PALP (Group 4). CisPt was administered intraperitoneally 9-times once every second day; CCDTHT was administered for 15 days once daily; and PALP was administered 3 times every $3^{rd}$ day. In each group 7 mice were included. The mean values±std. dev. for tumor volumes and body weights are shown in TABLE 9 and TABLE 10, respectively.

The results show that CCDTHT and PALP in combination significantly enhance the inhibitory effects of CisPt on the growth of MXT tumors (TABLE 9). In addition, CCDTHT alone, and particularly in combination with PALP, prevents the serious loss of body weight induced by CisPt (TABLE 10). Finally, the two agents together increased the survival time from 34 days, observed with CisPt alone, to 40 days.

TABLE 8

Combined inhibitory effects of CCDTHT and PALP on the growth of human leukemia xenografts.

| Group | Treatment | Tumor volume (cm³) | | | |
|---|---|---|---|---|---|
| | | Day 12 | Day 16 | Day 22 | Day 26 |
| 1 | None | 0.43 ± 0.21 | 1.55 ± 0.62 | 3.87 ± 0.59 | 5.73 ± 0.75 |
| 2 | CCDTHT | 0.46 ± 0.32 | 1.26 ± 0.73 | 2.74 ± 0.37 | 3.72 ± 0.44 |
| 3 | CCDTHT + PALP | 0.48 ± 0.20 | 0.88 ± 0.27 | 2.14 ± 0.72 | 3.07 ± 0.53 |

TABLE 9

CCDTHT and PALP in combination enhance the inhibitory effects of CisPt on the growth of MXT tumors.

| | | Tumor volume (cm³) | | | |
|---|---|---|---|---|---|
| Group | Treatment | Day 7 | Day 11 | Day 15 | Day 21 |
| 1 | None | 0.38 ± 0.13 | 2.21 ± 0.47 | 5.98 ± 0.76 | 12.66 ± 2.09 |
| 2 | CisPt | 0.36 ± 0.12 | 1.92 ± 0.67 | 3.80 ± 1.30 | 6.64 ± 1.28 |
| 3 | CisPt + CCDTHT | 0.40 ± 0.10 | 1.63 ± 0.24 | 3.16 ± 0.39 | 5.14 ± 0.71 |
| 4 | CisPt + CCDTHT + PALP | 0.41 ± 0.07 | 1.03 ± 0.12 | 2.40 ± 0.32 | 3.72 ± 0.53 |

TABLE 10

CCDTHT and PALP in combination prevent CisPt-induced loss of body weight.

| | | Body weight (g) | | | |
|---|---|---|---|---|---|
| Group | Treatment | Day 7 | Day 11 | Day 15 | Day 21 |
| 1 | None | 22.4 ± 0.60 | 24.06 ± 0.56 | 25.6 ± 0.65 | 27.4 ± 0.70 |
| 2 | CisPt | 22.2 ± 1.10 | 23.10 ± 1.40 | 22.9 ± 1.00 | 20.6 ± 1.80 |
| 3 | CisPt + CCDTHT | 22.5 ± 0.79 | 23.8 ± 0.54 | 24.1 ± 0.94 | 26.7 ± 0.97 |
| 4 | CisPt + CCDTHT + PALP | 22.0 ± 0.38 | 23.6 ± 0.79 | 25.4 ± 1.09 | 27.9 ± 0.75 |

What is claimed is:

1. A compound represented by the formula:

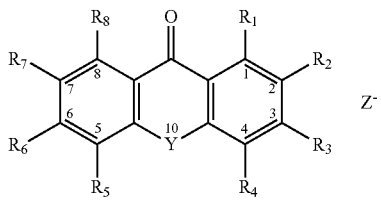

wherein $R_1$ and $R_{3-8}$ are independently hydrogen, $C_1$-$C_{26}$ straight, branched or cyclic alkanes or alkenes, aromatic hydrocarbons, alcohols, ethers, aldehydes, ketones, carboxylic acids, amines, amides, nitriles, or five- and/or six-membered heterocyclic moieties;

wherein $R_2$ is —$CH_2$—O-L-N+($R_{11}$, $R_{12}$, $R_{13}$); or —O—$CH_2$-L-N+($R_{11}$, $R_{12}$, $R_{13}$);

wherein Y is —S—, —Se—, —$CH_2$—, —NH— or —O—;

wherein L is a $C_1$-$C_4$ straight alkane, alkene, thiol, ether, or amine;

wherein $R_{11}$, $R_{12}$ and $R_{13}$ are independently $C_1$-$C_4$ straight alkanes, alkenes, thiols, amines, ethers or alcohols;

wherein $Z^-$ is $Cl^-$, $Br^-$ or $I^-$; and wherein the compound may be administered in a suitable carrier at a therapeutically effective dose to an untreated or treated mammal or human with cancer to reduce tumor size or to treat loss of lean body weight as a consequence of composition-induced reduction in tumor size, or both.

2. The compound of claim 1 wherein $R_{11}$, $R_{12}$, and $R_{13}$ are independently methyl, ethyl, propyl, allyl, ether, sulfhydryl, amino or OH groups.

3. The compound of claim 1 wherein the heterocyclic compound is a thioxanthone and $R_2$ is —$CH_2$—O-L-N+($R_{11}$, $R_{12}$, $R_{13}$).

4. The compound of claim 3 wherein the compound is N,N,-diethyl-N-methyl-2-((9-oxo-9H-thioxanthen-2-yl)methoxy)-ethanaminium iodide.

5. The compound of claim 3, wherein the compound is N,N,N-trimethyl-2-((9-oxo-9H-thioxanthen-2-yl)methoxy)-ethanaminium iodide.

6. The compound of claim 3, wherein the compound is N-ethyl-N,N-dimethyl-2-((9-oxo-9H-thioxanthen-2-yl)methoxy)-ethanaminium iodide.

7. The composition of claim 3, wherein the compound is 2 Hydroxy-N,N-dimethyl-N-((9-oxo-9H-thioxanthen-2-yl)methyl)-ethanaminium bromide.

8. A method of synthesizing a compound having the following generic formula:

Formula I wherein L is a $C_1$-$C_4$ straight alkane; wherein $R_1$, $R_2$ and $R_3$ are independently hydrogen or a $C_1$-$C_4$ straight alkane; and wherein $Z^-$ is $Cl^-$ or $I^-$, the method comprising the steps of:

a) contacting 2'-iodobenzoic acid with p-thiocresol to form 2-((4-methylphenyl)thio)-benzoic acid;

b) heating 2-((4-methylphenyl)thio)-benzoic acid in the presence of polyphosphoric acid to form 2-methyl-9H-thioxanthen-9-one, c) contacting 2-methyl-9H-thioxanthen-9-one with a source of bromide to form 2-(bromomethyl)-9H-thioxanthen-9-one;

d) contacting 2-(bromomethyl)-9H-thioxanthen-9-one with 2'-dialkyl aminoethanol or 2' dialkyl aminopropanol to form 2-{(2-(dialkylamino)ethoxy)methyl}-9H-thioxanthen-9-one or 2-{(2-(dialkylamino)propoxy)methyl}-9H-thioxanthen-9-one; and e) contacting 2-{(2-(dialkylamino)ethoxy)methyl}-9H-thioxanthen-9-one or 2-{(2-(dialkylamino)propoxy)methyl}-9H-thioxanthen-9-one with an alkyl iodide or an alkyl chloride to form a compound having the formula of Formula I.

9. A compound represented by the formula:

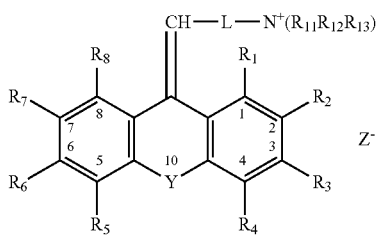

wherein $R_1$ and $R_{3-8}$ are independently hydrogen, $C_1$-$C_{26}$ straight, branched or cyclic alkanes or alkenes, aromatic hydrocarbons, alcohols, ethers, aldehydes, ketones, carboxylic acids, amines, amides, nitriles, or five- and/or six-membered heterocyclic moieties;
wherein $R_2$ is hydrogen or —$CH_3$;
wherein Y is —S—, —Se—, —NH—, or —O—;
wherein L is a $C_1$-$C_4$ straight alkane, alkene, thiol, ether, or amine;
wherein $R_{11}$, $R_{12}$ and $R_{13}$ are independently $C_1$-$C_a$ straight alkanes, alkenes, thiols, amines, ethers or alcohols;
wherein $Z^-$ is $Cl^-$, $Br^-$ or $I^-$; and
wherein the compound may be administered in a suitable carrier at a therapeutically effective dose to an untreated or treated mammal or human with cancer to reduce tumor size or to treat loss of lean body weight as a consequence of composition-induced reduction in tumor size or both.

10. The composition of claim 9 wherein the heterocyclic compound is a thioxanthene and wherein $R_2$ is —$CH_3$ or hydrogen, L is —$(CH_2)_2$—, and $R_1$, $R_3$-$R_8$ are hydrogen.

11. The composition of claim 9 wherein the heterocyclic compound is N,N-diethyl-N-allyl-3-(2-methyl-9H-thioxanthen-9-ylidene)-propane-1-aminium bromide.

12. The composition of claim 9 wherein the heterocyclic compound is N,N,N-trimethyl-3-(2-methyl-9H-thioxanthen-9-ylidene)-propane-1-aminium iodide.

13. The composition of claim 9 wherein the heterocyclic compound is N,N,N-trimethyl-3-(9H-thioxanthen-9-ylidene)-propane-1-aminium iodide.

14. The composition of claim 9 wherein the heterocyclic compound is N,N,N-trimethyl-3-(9H-selenoxanthen-9-ylidene)-propane-1-aminium iodide.

15. A method of synthesizing a compound having the following generic formula:

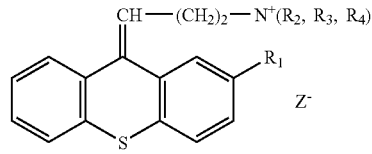

Formula II wherein $R_1$ is hydrogen or —$CH_3$; wherein $R_2$, $R_3$ and $R_4$ are each independently $C_1$-$C_4$ straight alkanes or alkenes; and wherein $Z^-$ is $Cl^-$, $Br^-$ or $I^-$, the method comprising the steps of:

a) reacting thioxanthone or 2-methylthioxanthone with a reagent formed by reacting magnesium with dibromide methane and an dialkylaminopropyl chloride to form 9-(3-(dialkylamino)propyl)-9H-thioxanthen-9-ol or 9-(3-(dialkylamino)propyl)-2-methyl-9H-thioxanthen-9-ol;

b) refluxing with constant mixing of 9-(3-(dialkylamino)propyl)-9H-thioxanthen-9-ol or 9-(3-(dialkylamino)propyl)-2-methyl-9H-thioxanthen-9-ol in the presence of an aqueous acid to form N,N-dialkyl-N-(3-(9H-thioxanthen-9-ylidene)-propyl amine or N,N-dialkyl-N-(3-(2-methyl-9H-thioxanthen-9-ylidene)-propyl amine; and c) contacting N,N-dialkyl-N-(3-(9H-thioxanthen-9-ylidene)-propyl amine or N,N-dialkyl-N-(3-(2-methyl-9H-thioxanthen-9-ylidene)-propyl amine with a halide compound having the structure R—X, wherein R is an alkyl or allyl group and X is either $Cl^-$, $Br^-$ or $I^-$ to form a compound having the formula of Formula II.

16. The compound of claims 1 or 9 combined with a suitable carrier to form a tablet, gel capsule, or a liquid that is administered via oral delivery.

17. The compound of claims 1 or 9 combined with 0.9% sodium chloride and administered via an injection or infusion delivery.

* * * * *